(12) United States Patent
Lyras et al.

(10) Patent No.: US 10,144,775 B2
(45) Date of Patent: Dec. 4, 2018

(54) **METHODS AND COMPOSITIONS FOR THE TREATMENT AND/OR PROPHYLAXIS OF *CLOSTRIDIUM DIFFICILE* ASSOCIATED DISEASE**

(71) Applicant: IMMURON LIMITED, Blackburn North, Victoria (AU)

(72) Inventors: Dena Lyras, Heidelberg Heights (AU); Melanie Hutton, South Yarra (AU); Bliss Cunningham, Dandenong North (AU); Lucy Li, Wheelers Hill (AU); Glen Carter, Point Cook (AU); Julian Rood, Bentleigh (AU)

(73) Assignee: IMMURON LIMITED, Southbank, Victoria (AU)

( * ) Notice: Subject to any disclaimer, the term of this patent is extended or adjusted under 35 U.S.C. 154(b) by 0 days.

(21) Appl. No.: 14/785,527

(22) PCT Filed: Apr. 17, 2014

(86) PCT No.: PCT/AU2014/000447
§ 371 (c)(1),
(2) Date: Oct. 19, 2015

(87) PCT Pub. No.: WO2014/169344
PCT Pub. Date: Oct. 23, 2014

(65) Prior Publication Data
US 2016/0083457 A1    Mar. 24, 2016

(30) Foreign Application Priority Data
Apr. 19, 2013 (AU) ................ 2013901386

(51) Int. Cl.
*C07K 16/12* (2006.01)
*A61K 9/00* (2006.01)
*A61K 39/00* (2006.01)

(52) U.S. Cl.
CPC ........ *C07K 16/1282* (2013.01); *A61K 9/0053* (2013.01); *A61K 2039/505* (2013.01); *A61K 2039/522* (2013.01); *C07K 2317/12* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 4,550,019 A | 10/1985 | Polson | |
| 4,748,018 A | 5/1988 | Stolle et al. | |
| 6,537,500 B1 | 3/2003 | Brenner et al. | |
| 2004/0161427 A1 | 8/2004 | Nash et al. | |

FOREIGN PATENT DOCUMENTS

| | | |
|---|---|---|
| WO | WO 2003/080082 A1 | 10/2003 |
| WO | WO 2004/078209 A1 | 9/2004 |
| WO | WO 2006/053383 A1 | 5/2006 |
| WO | WO 2012/092469 A2 | 7/2012 |

OTHER PUBLICATIONS

Sebaihia et al. (Nature Gen., 38:779-786, 2006).*
Belmares et al. (Clin. Infect. Dis., 49:1141-1147, 2009).*
Calabi et al., "Molecular characterization of the surface layer proteins from *Clostridium difficile*," Mol. Microbiol. 40:1187-1199 (2001).
Holliger et al., ""Diabodies": Small bivalent and bispecific antibody fragments," PNAS USA 90:6444-6448 (1993).
Kipriyanov et al., "Recombinant Single-Chain Fv Fragments Carrying C-Terminal Cysteine Residues: Production of Bivalent and Biotinylated Miniantibodies," Molecular Immunology 31(14):1047-1058 (1994).
Lyras et al., "Toxin B is essential for virulence of *Clostridium difficile*," Nature 458(7242): 1176-1179 (2009).
Poljak et al., "Production and structure of diabodies," Structure 2:1121-1123 (1994).
Australian Patent Office, International Search Report in International Application No. PCT/AU2014/000447 (dated Jul. 15, 2014).
Australian Patent Office, Written Opinion in International Application No. PCT/AU2014/000447 (dated Jul. 15, 2014).
International Bureau of WIPO, International Preliminary Report on Patentability in International Application No. PCT/AU2014/000447 (dated Oct. 20, 2015).
Akita et al., "Comparison of four purification methods for the production of immunoglobulins from eggs laid by hens immunized with an enterotoxigenic *E. coli* strain," J. Immunol. Methods 160(2):207-214 (1993).
Kipriyanov et al., "Single-chain antibody streptavidin fusions: tetrameric bifunctional scFv-complexes with biotin binding activity and enhanced affinity to antigen," Human Antibodies and Hybridomas 6(3):93-101 (1995).
Kuehne et al., "The role of toxin A and toxin B in *Clostridium difficile* infection," Nature 467:711-714 (2010).
Remington's Pharmaceutical Sciences, 18th Edition, AR Gennaro, Editor, Mack Publishing Co., Easton, PA (1990), pp. 1521-1712.

* cited by examiner

Primary Examiner — Brian Gangle
(74) Attorney, Agent, or Firm — Leydig, Voit & Mayer, Ltd.

(57) ABSTRACT

The present invention relates to methods and compositions for the treatment and/or prophylaxis of *Clostridium difficile* associated disease (CD AD). In particular, the invention relates to antibodies that bind to *C. difficile* antigens and are capable of inhibiting *C. difficile* infection, at least one symptom of *C. difficile* associated disease, shedding of *C. difficile*, and *C. difficile* associated mortality. The compositions of the present application comprise: mammalian or avian antibodies which bind to a *C. difficile* Toxin B; and mammalian or avian antibodies that bind to a *C. difficile* vegetative cell antigen and/or a *C. difficile* endospore antigen.

38 Claims, 19 Drawing Sheets

Figure 1
Trial #1
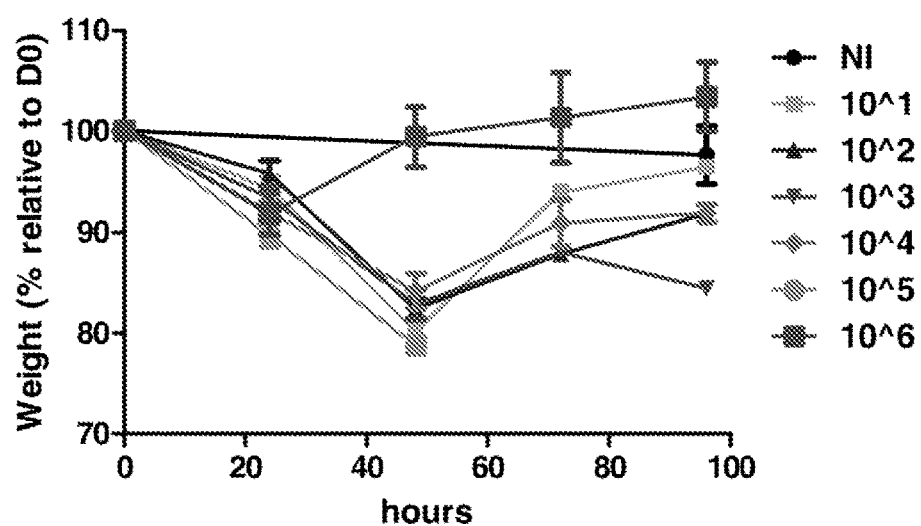
Trial #2
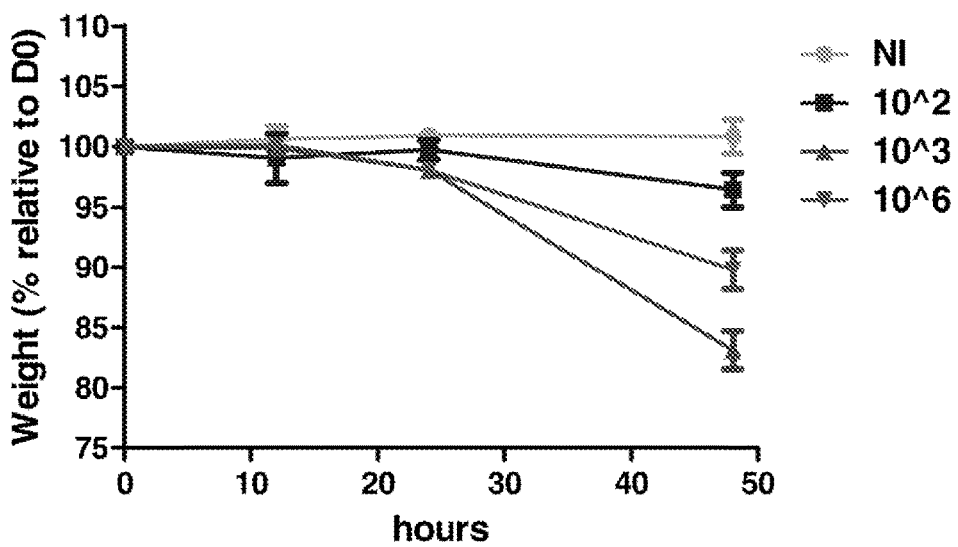

Figure 2
Trial #1
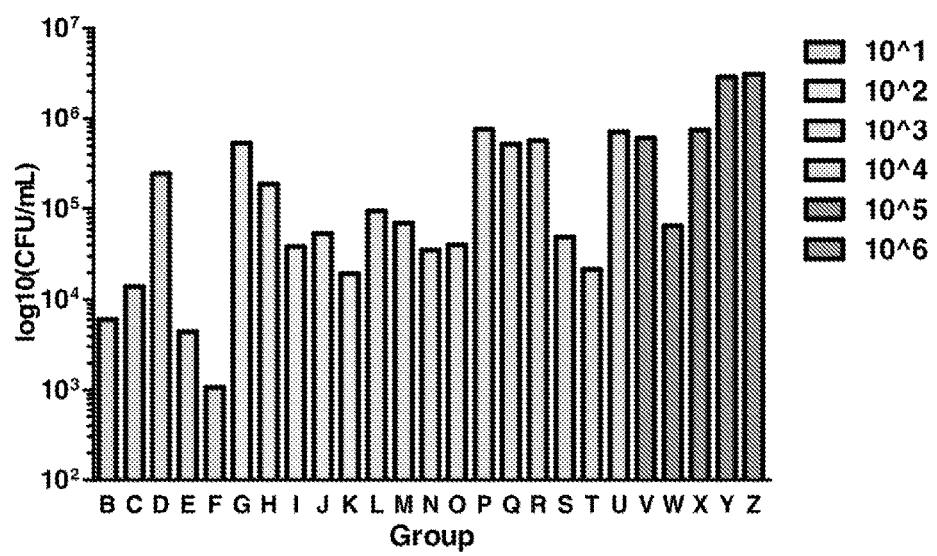
Trial #2
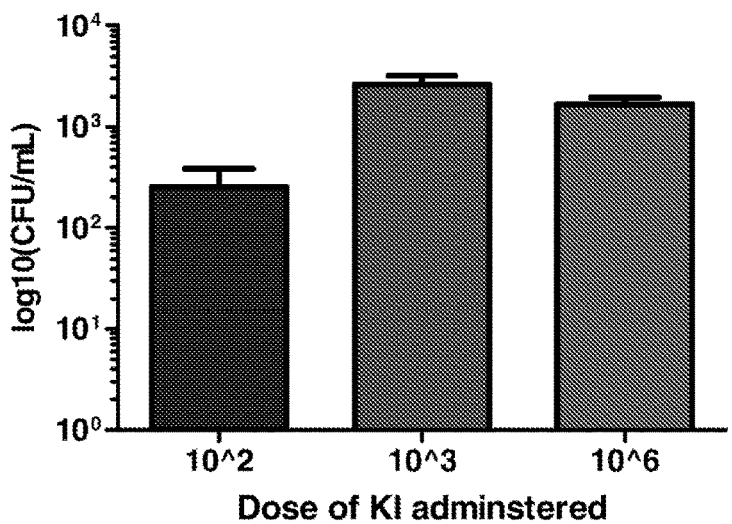

Total IgG concentration in bovine colostrum powder

| Cow number | Antigen | IgG concentration in colostrum powder (mg of IgG/g colostrum) |
|---|---|---|
| 7017 | Non-immune | 365 mg/g |
| 7009 | Toxin B | 199 mg/g |
| 7028b | Toxin B | 253 mg/g |
| 7010 | Toxin B | 415 mg/g |

Figure 8

Figure 13
A
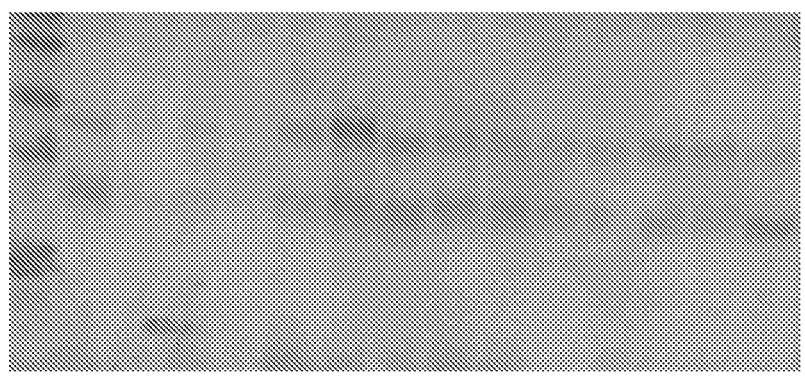
Pre-bleed
B
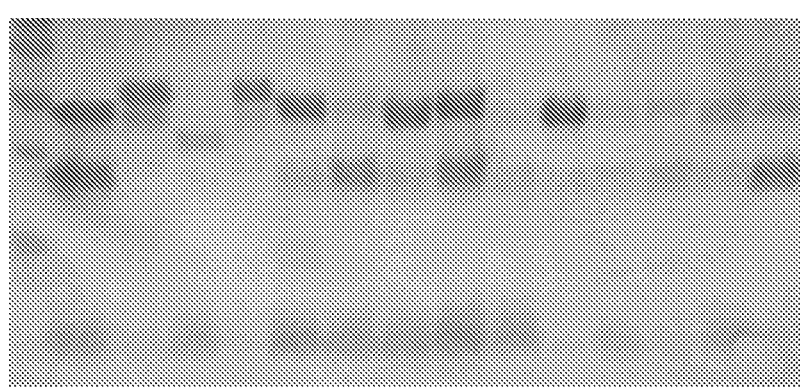
Third bleed

Figure 15
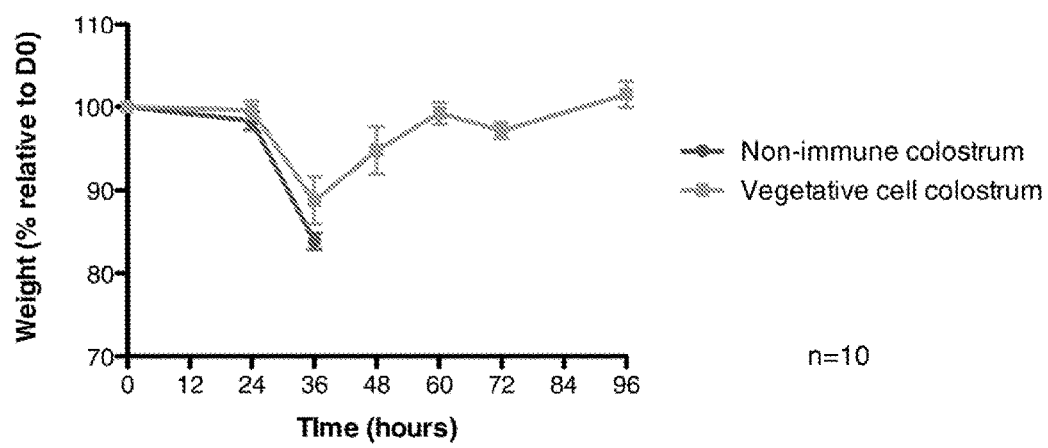
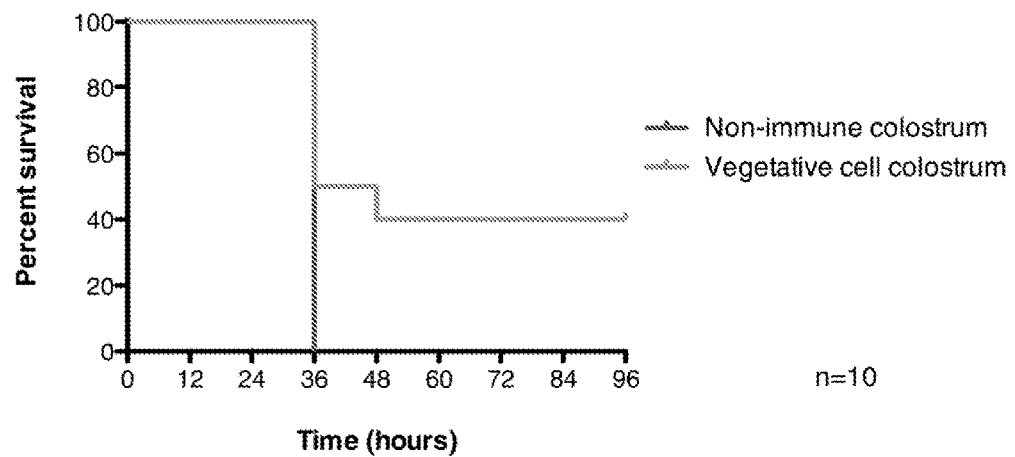

Figure 18

METHODS AND COMPOSITIONS FOR THE TREATMENT AND/OR PROPHYLAXIS OF *CLOSTRIDIUM DIFFICILE* ASSOCIATED DISEASE

CROSS-REFERENCE TO RELATED APPLICATIONS

The patent application is the U.S. national phase of International Application No. PCT/AU2014/000447, filed on Apr. 17, 2014, which claims the benefit of Australian Patent Application No. 2013901386, filed Apr. 19, 2013, the disclosures of which are incorporated herein by reference in their entireties for all pruposes.

TECHNICAL FIELD

The present invention relates to methods and compositions for the treatment and/or prophylaxis of *Clostridium difficile* associated disease (CDAD). In particular, the invention relates to antibodies that bind to *C. difficile* antigens and are capable of inhibiting *C. difficile* infection, at least one symptom of *C. difficile* associated disease, shedding of *C. difficile*, and *C. difficile* associated mortality.

BACKGROUND OF INVENTION

*C. difficile* is a Gram-positive anaerobic bacterium that is one of the most important causes of antibiotic-associated diarrhoea in the developed world, leading to significant morbidity and mortality and placing a considerable economic burden on healthcare systems. Occurrence of diarrhoea in hospitalised patients who receive antibiotics ranges from 3% to 29%. *C. difficile* has been implicated as the causative organism in 10-25% of patients with antibiotic-associated diarrhoea, 50-75% of those with antibiotic-associated colitis, and 90-100% of those with antibiotic-associated pseudomembranous colitis.

The organism causes a range of intestinal diseases collectively referred to as *C. difficile* infections (CD) or *C. difficile* associated disease (CDAD). This disease can range from mild self-limiting diarrhoea, through to moderately severe diarrhoea that can lead to more serious complications including pseudomembraneous colitis and toxic megacolon, which is fatal in approximately one-third of afflicted patients. Unlike other enteric pathogens, disease is almost always associated with antimicrobial therapy or an alteration to the endogenous gastrointestinal microbiota. Mortality of *C. difficile*-associated disease ranges from 6% to 30% when pseudomembranous colitis is shown to be present and is substantial even in the absence of colitis.

Although CDAD has been an ongoing problem in hospitals since the introduction of antibiotics, there has been an astonishing increase in the rate and prevalence of CDI in the past decade, resulting in major epidemics in many parts of the world, including the UK, USA, Canada and mainland Europe. Furthermore, the proportion of patients who have severe, refractory, or recurrent disease has increased over the last decade.

These worldwide epidemics are largely due to the emergence of strains of increased virulence, or 'hypervirulent' isolates, belonging to the BI/NAP1/027 category. These strains are resistant to fluoroquinolones, and are associated with more severe disease and higher mortality rates. *C. difficile* now also causes disease in those previously not at risk, such as children and pregnant women, with community-associated *C. difficile* disease being increasingly common.

Treatment of CDAD has historically involved the use of vancomycin, metronidazole, and a combination of vancomycin and metronidazole, however there have been notable treatment failures and recurrences in a large number of published studies of antibiotic efficacy.

Importantly, CDAD recurs after treatment in 8-50% of cases.

Accordingly, there remained significant problems to be overcome in the design of an efficacious treatment for *C. difficile* associated disease. It is an aspect of the present invention to provide compositions and methods for the prevention and treatment of CDAD.

SUMMARY OF INVENTION

In a first aspect, the present invention provides a composition comprising mammalian or avian antibodies for use in the treatment and/or prophylaxis of at least one symptom of *Clostridium difficile* associated disease, wherein the antibodies comprise: a) antibodies that bind to a *Clostridium difficile* Toxin B; and b) antibodies that bind to at least one *Clostridium difficile* vegetative cell antigen, and/or antibodies that bind to at least one *Clostridium difficile* endospore antigen.

In a second aspect, the present invention provides a method for the treatment and/or prophylaxis of at least one symptom of *Clostridium difficile* associated disease in a subject, said method comprising administering to the subject a composition comprising mammalian or avian antibodies, wherein the antibodies comprise: a) antibodies that bind to a *Clostridium difficile* Toxin B; and b) antibodies that bind to at least one *Clostridium difficile* vegetative cell antigen, and/or antibodies that bind to at least one *Clostridium difficile* endospore antigen In one embodiment, the antibodies are polyclonal antibodies.

In one embodiment, the antibodies that bind to a *Clostridium difficile* Toxin B are raised against a vaccine comprising a first strain Toxin B of a first strain of *Clostridium difficile*. The vaccine may comprise *Clostridium difficile* strain 630 Toxin B.

In another embodiment, the antibodies that bind to a *Clostridium difficile* Toxin B bind to a Toxin B of a second strain of *Clostridium difficile*.

In a further embodiment, the antibodies that bind to at least one *Clostridium difficile* vegetative cell antigen are raised against a vaccine comprising vegetative cells of a first strain of *Clostridium difficile*. The vaccine may comprise *Clostridium difficile* S-layer preparations. In another embodiment, the antibodies bind to SlpA.

In one embodiment, the antibodies that bind to at least one *Clostridium difficile* vegetative cell antigen bind to at least one *Clostridium difficile* vegetative cell antigen of a second strain of *Clostridium difficile*.

In another embodiment, the antibodies that bind to at least one *Clostridium difficile* endospore antigen are raised against a vaccine comprising endospores of a first strain of *Clostridium difficile*. In one embodiment, the vaccine comprises *Clostridium difficile* strain KI endospores. In another embodiment, the antibodies bind to exosporium proteins.

In another embodiment the vaccine is a mixture of endospores and vegetative cells.

In a further embodiment, the antibodies that bind to at least one *Clostridium difficile* endospore antigen bind to at least one endospore antigen of a second strain of *Clostridium difficile*.

In one embodiment, the antibodies are derived from hyperimmune material. In another embodiment, the antibodies are derived from bovine hyperimmune colostrum.

In one embodiment the hyperimmune material is prepared by vaccination of a first lot of one or more mammals with a vaccine comprising *Clostridium difficile* Toxin B, and vaccination of a second lot of one or more mammals with a vaccine comprising *Clostridium difficile* vegetative cells and/or vaccination of a third lot of one or more mammals with a vaccine comprising *Clostridium difficile* endospores, and subsequently blending the hyperimmune material from the lots.

In a further embodiment the composition is formulated for oral administration.

In one embodiment the composition is formulated for administration at a dose of about 30 mg to about 10000 mg per day, or formulated for administration at a dose of about 1800 mg per day.

In one embodiment the composition is administered at a dose of about 30 mg to about 10000 mg per day, or administered at a dose of about 1800 mg per day.

In one embodiment, the composition is administered prior to an increased risk of acquiring *C. difficile* infection. In another embodiment the composition is administered prior to admission to hospital or a nursing home. In further embodiments, the composition is administered for at least 3 days prior to an increased risk of acquiring *C. difficile* infection, at least 5 days prior to an increased risk of acquiring *C. difficile* infection or at least 7 days prior to an increased risk of acquiring *C. difficile* infection.

In another embodiment, the at least one symptom of *Clostridium difficile* associated disease is selected from the group consisting of diarrhea, abdominal pain, fever, loss of appetite, pseudomembranous colitis, cytotoxic megacolon, *C. difficile* colonisation, weight loss, cytotoxicity, gastrointestinal damage, histopathologic change in the gastrointestinal tract, faecal shedding of *C. difficile* spores, and *C. difficile* associated mortality.

A reference herein to a patent document or other matter which is given as prior art is not to be taken as an admission that the document or matter was known or that the information it contains was part of the common general knowledge as at the priority date of any of the claims.

BRIEF DESCRIPTION OF DRAWINGS

FIG. 1: Infection of mice with *C. difficile* endospores results in *C. difficile* associated disease.

Results show weight loss in groups of three C57/BL6 mice infected orally with $10^1$, $10^2$, $10^3$, $10^4$, $10^5$ or $10^6$ endospores generated from the *C. difficile* KI strain. Mice showed *C. difficile* associated disease, as measured by weight loss following infection.

FIG. 2: Infection of mice with *C. difficile* endospores results in colonisation with *C. difficile* and faecal shedding of *C. difficile*.

Results show faecal shedding of *C. difficile* spores in groups of three C57/BL6 mice infected orally with $10^1$, $10^2$, $10^3$, $10^4$, $10^5$ or $10^6$ endospores generated from the *C. difficile* KI strain. Mice showed measurable colonisation, as measured by faecal shedding, following infection.

Figure 3:
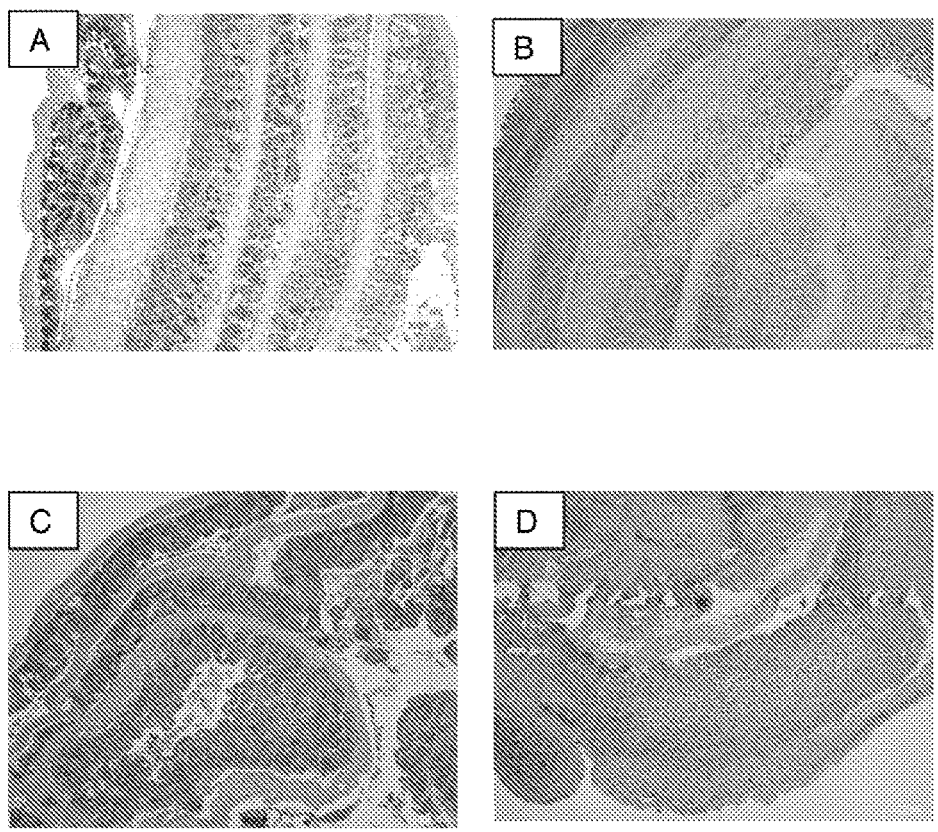

FIG. 3: Infection of mice with *C. difficile* endospores results in gastrointestinal damage in the caecum and colon during infection.

Results show histopathologic change in the caecum and colon of C57/BL6 mice 48 hours following infection with $10^3$ endospores generated from the *C. difficile* KI strain. A—Non-infected control mouse colon; B—Mouse colon of mouse infected with $10^3$ spores; C—Non-infected control mouse caecum; D—Mouse caecum of mouse infected with $10^3$ spores. Tissues were stained with PAS/Alcian blue. Histopathologic damage was demonstrated in the caecum and colon 48 hours following infection.

Figure 4:
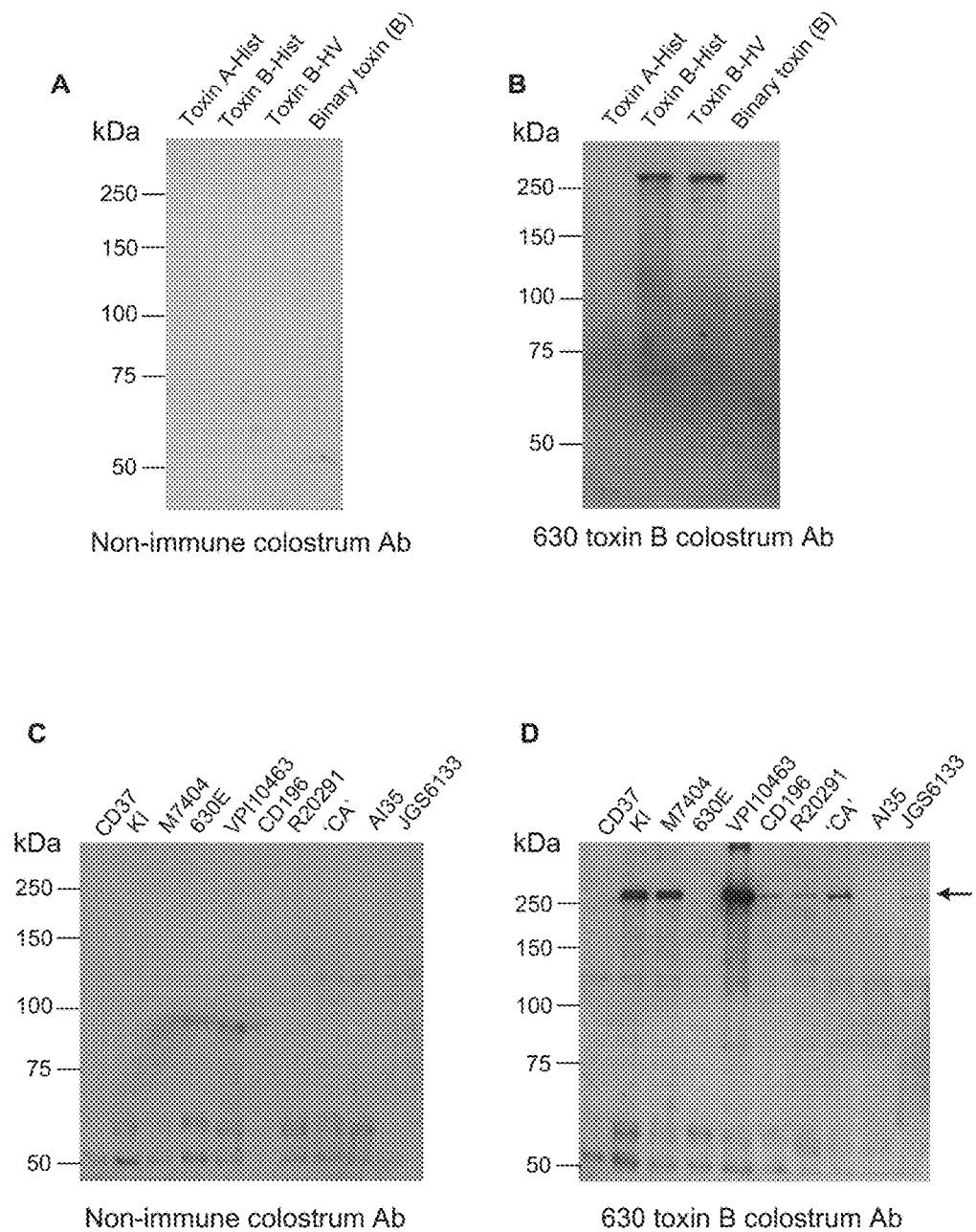

FIG. 4: Detection of antibodies that bind to *C. difficile* Toxin B in bovine hyperimmune colostrum, and demonstration that antibodies that bind to *C. difficile* Toxin B of a first strain bind to Toxin B of a second strain.

Results show hyperimmune colostrum derived from cows vaccinated with Toxin B from *C. difficile* strain 630 comprises antibodies that bind to Toxin B. A—Non-immune colostrum does not contain antibodies that bind to commercial purified historical Toxin A (Toxin A-Hist), purified historical Toxin B (Toxin B-Hist) or purified hypervirulent strain 027 Toxin B (Toxin B-HV); B—Colostrum derived from cows vaccinated with Toxin B from *C. difficile* strain 630 comprises antibodies that bind to purified historical Toxin B (Toxin B-Hist) and hypervirulent strain 027 Toxin B (Toxin B-HV), but not Toxin A.

Results also show hyperimmune colostrum derived from cows vaccinated with Toxin B from *C. difficile* strain 630 comprises antibodies that bind to Toxin B of different *C. difficile* strains. C—Non-immune colostrum does not contain antibodies that bind to commercial purified historical Toxin A (Toxin A-Hist), purified historical Toxin B (Toxin B-Hist) or purified hypervirulent strain 027 Toxin B (Toxin B-HV); D—Colostrum derived from cows vaccinated with Toxin B from *C. difficile* strain 630 comprises antibodies that bind to purified historical Toxin B (Toxin B-Hist) and hypervirulent strain 027 Toxin B (Toxin B-HV), but not Toxin A.

Figure 5:
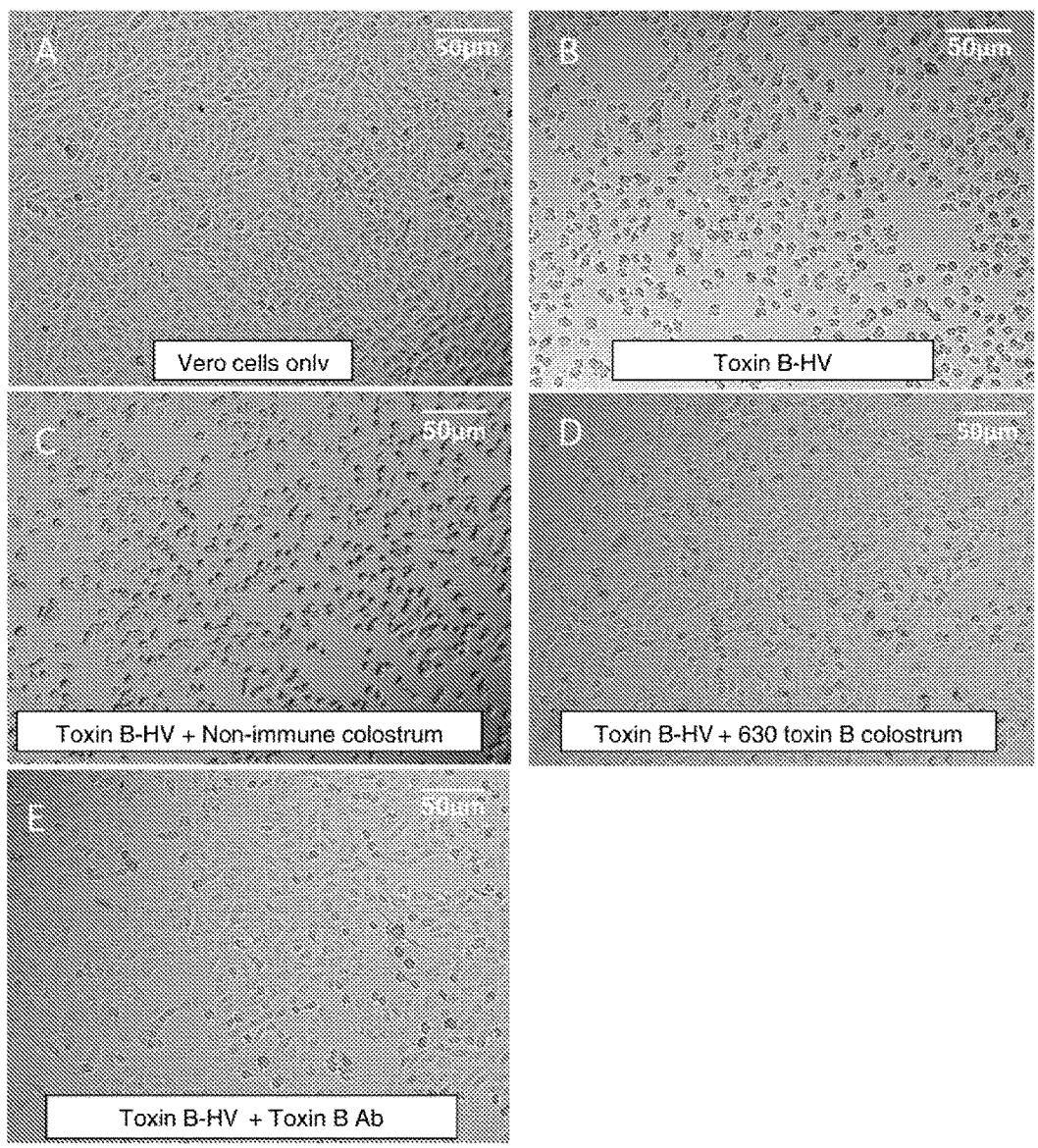

FIG. 5: Antibodies that bind to *C. difficile* Toxin B neutralise Toxin B cytotoxicity to cells, and demonstration that antibodies that bind to *C. difficile* Toxin B of a first strain neutralise cytotoxicity of Toxin B of a second strain.

Results show photomicrographs taken of Vero cells after exposure to toxin with or without prior incubation with colostrum IgG antibodies. Panel A shows Vero cells not exposed to TcdB-HV; B, Vero cells exposed to TcdB-HV; C, Vero cells that were exposed to toxin that had been pre-incubated with purified IgG from non-immune colostrum; D, Vero cells that were exposed to toxin that had been pre-incubated with 630 Toxin B colostrum antibodies and E, Vero cells that were exposed to toxin that had been pre-incubated with commercial anti-Toxin B antibody; Cell death is seen by cell rounding. Results show hyperimmune colostrum derived from cows vaccinated with Toxin B from *C. difficile* strain 630 comprises antibodies that bind to and inhibit the cytotoxicity of Toxin B. The results also show that colostrum derived from cows vaccinated with Toxin B from *C. difficile* strain 630 comprises antibodies that bind to and inhibit the cytotoxicity of Toxin B from a hypervirulent 027 strain.

Figure 6:
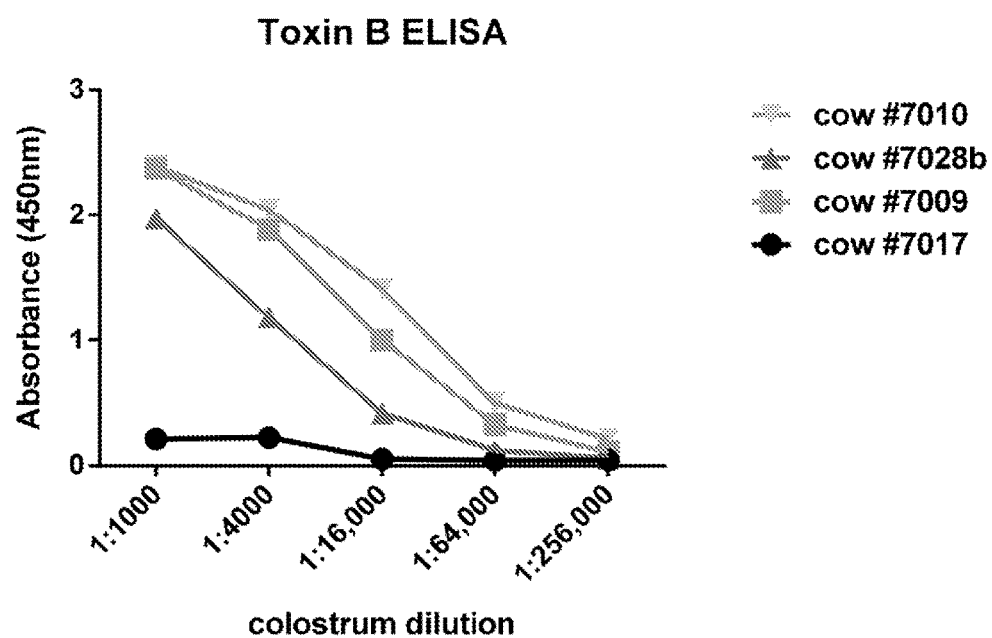

FIG. 6. Detection of total concentration of IgG in bovine hyperimmune colostrum prepared using a recombinant Toxin B vaccine and detection of antibodies that bind to *C. difficile* Toxin B in bovine hyperimmune colostrum prepared using a recombinant Toxin B vaccine.

A. Results show hyperimmune colostrum derived from cows vaccinated with recombinant Toxin B from *C. difficile* strain 630 comprises IgG antibodies. Colostrum from a non-immune cow (#7017) as well as colostrum from cows #7009, #7010 and #7028b (all *C. difficile* strain 630 recombinant Toxin B) was prepared and the total concentration of IgG in each sample was determined by IgG ELISA. The results show the IgG concentration (in mg) per 1 g of bovine colostrum powder. The results show that the non-immune colostrum (cow #7017) has an IgG concentration of 365 mg/g, whereas cows #7009, #7028b and #7010 have total IgG. concentrations of 199 mg/g, 253 mg/g and 415 mg/g, respectively. B. Results show hyperimmune colostrum derived from cows vaccinated with *C. difficile* strain 630 recombinant Toxin B comprises antibodies that bind to *C. difficile* 630 recombinant Toxin B. Colostrum from a non-immune cow (#7017) as well as colostrum from cows #7009, #7010 and #7028b (all *C. difficile* strain 630 recombinant Toxin B) was prepared and the presence of specific anti-Toxin B antibodies was confirmed by ELISA. For this, wells were coated with 1 µg/mL recombinant Toxin B/well and incubated with 4-fold serial dilutions (starting from 1:1000 dilution of colostrum of either non-immune or Toxin B colostrum. The results show the antibody titre for the non-immune colostrum was less than 4000, the antibody titre for cow #7028b was 64,000 and the titres for both cow #7009 and #7010 colostrum batches was greater than 256, 000. The results show that colostrum derived from cows vaccinated with Toxin B from *C. difficile* strain 630 comprises antibodies that bind to Toxin B.

Figure 7:
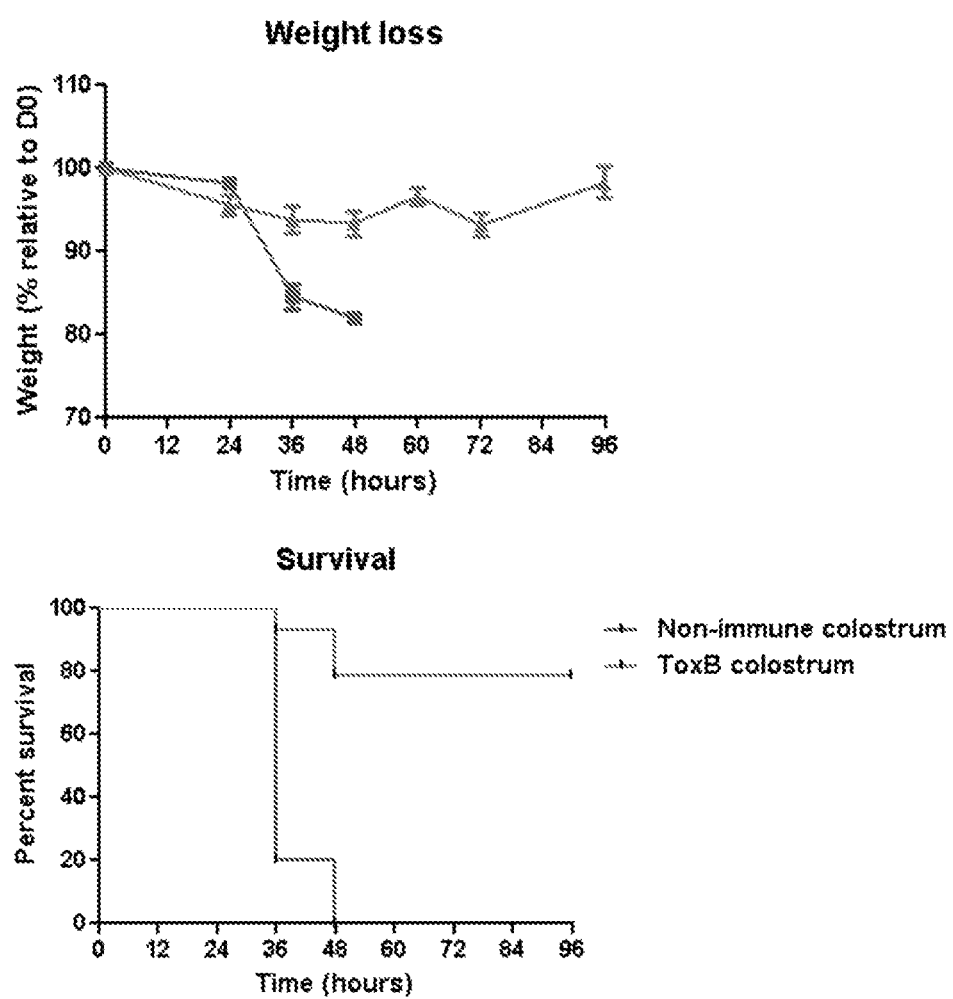

FIG. 7: Administration of antibodies that bind to *C. difficile* Toxin B is effective for preventing *C. difficile* associated weight loss and *C. difficile* associated mortality.

Groups of male, 6-7 week old, C57/BL6 mice were pre-treated with an antibiotic cocktail for 7 days. Mice were administered either non-immune or Toxin B colostrum (in the drinking water) for 2 days prior to infection with *C. difficile* KI endospores ($10^3$ spores/mouse). Mice were kept on colostrum during the course of the trial and monitored for weight loss and survival. Data is pooled from three independent mouse trials. N≥14 mice/group. Results show hyperimmune colostrum derived from cows vaccinated with Toxin B from *C. difficile* strain 630 comprises antibodies are effective in treating weight loss associated with *C. difficile* infection. Results also show hyperimmune colostrum derived from cows vaccinated with Toxin B from *C. difficile* strain 630 comprises antibodies are highly effective in preventing *C. difficile* associated mortality.

Figure 8:
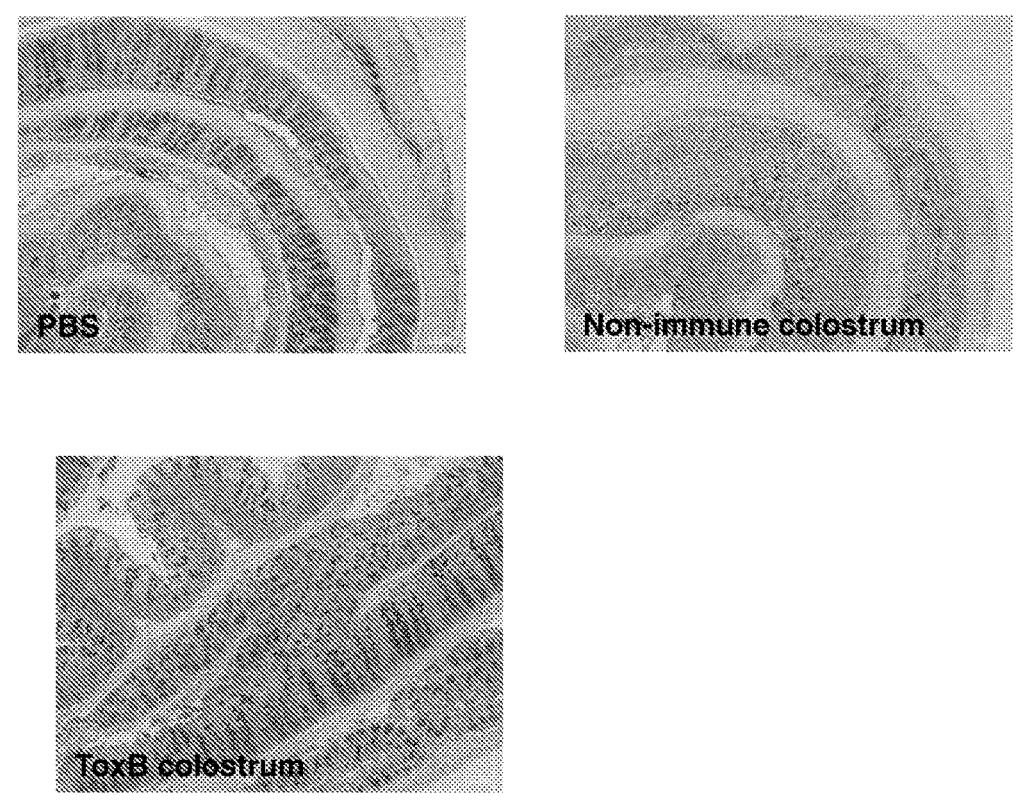

FIG. 8: Administration of antibodies that bind to *C. difficile* Toxin B in bovine hyperimmune colostrum is effective for preventing *C. difficile* associated gastrointestinal damage.

Results show hyperimmune colostrum derived from cows vaccinated with Toxin B from *C. difficile* strain 630 comprises antibodies are effective in treating histopathologic damage associated with *C. difficile* infection. Groups of male, 6-7 week old, C57/BL6 mice were pre-treated with an antibiotic cocktail for 7 days. Mice were administered either non-immune or Toxin B colostrum (in the drinking water) for 2 days prior to infection with *C. difficile* KI endospores ($10^3$ spores/mouse). Mice were kept on colostrum during the course of the trial and the colon and caecum of mice were collected and analysed for histopathologic damage. Data is pooled from three independent mouse trials. N≥14 mice/group. Representative images of sections of tissue are shown stained with PAS/alcian blue. Results demonstrate mice given non-immune colostrum displayed severely damaged colonic tissue compared to the mice that were given antibodies that bind to *C. difficile* Toxin B in bovine hyperimmune colostrum prior to infection or the uninfected (PBS) control mice. These results indicate that antibodies that bind to *C. difficile* Toxin B in bovine hyperimmune colostrum are effective in neutralising the activity of Toxin B in vivo, thereby preventing damage to the gastrointestinal tract of pre-treated mice.

Figure 9:
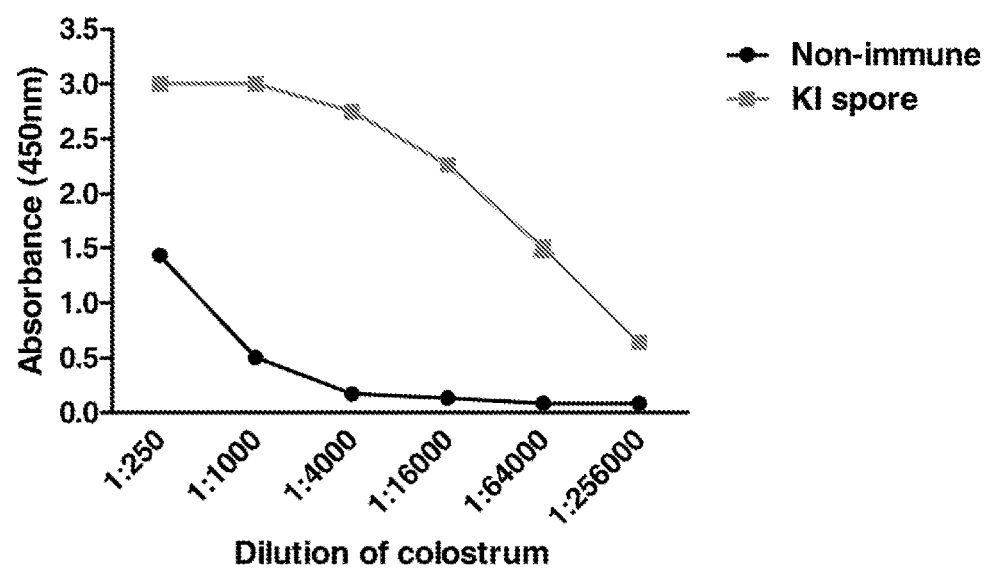

FIG. 9: Detection of antibodies that bind to *C. difficile* endospores in bovine hyperimmune colostrum prepared using an endospore vaccine.

Results show hyperimmune colostrum derived from cows vaccinated with *C. difficile* strain KI endospores comprises antibodies that bind to *C. difficile* endospores. Colostrum from cow #7003 (KI spore) was prepared and the presence of specific anti-endospore antibodies was confirmed by ELISA. For this, wells were coated with $10^4$ KI endospores/well and incubated with 4-fold serial dilutions (starting from 1:250 dilution of colostrum of either non-immune or KI spore colostrum. The results show the antibody titre for the KI spore colostrum was greater than 256,000.

Figure 10:
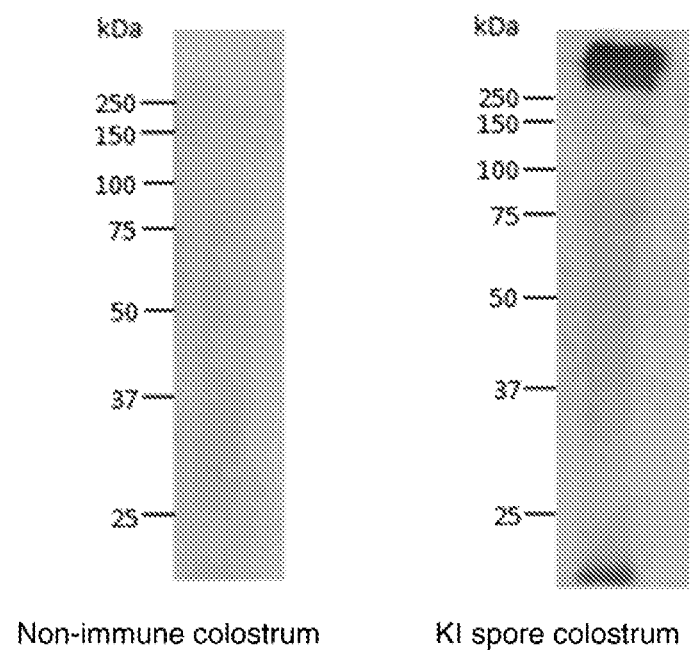

FIG. 10: Detection of antibodies that bind to *C. difficile* endospores and antibodies that bind to *C. difficile* exosporium proteins.

Colostrum derived from cows vaccinated with KI endospores was examined for its ability to bind to KI exosporium proteins. Exosporium from strain KI was extracted, fractioned using SDS-PAGE, transferred onto nitrocellulose membranes and subsequently probed with colostrum from an unimmunised cow or a cow vaccinated with KI endospores. FIG. 4 shows the colostrum from the vaccinated cow contained antibodies that could bind to exosporium proteins of *C. difficile* KI endospores (FIG. 4B). In contrast, there were no antibodies in the non-immune colostrum capable of binding exosporium proteins, suggesting that the KI spore colostrum contains antibodies specific to the KI spore surface. These results also show hyperimmune colostrum derived from cows vaccinated with endospores from *C. difficile* strain KI comprises antibodies that bind to exosporium proteins of *C. difficile*.

Figure 11:
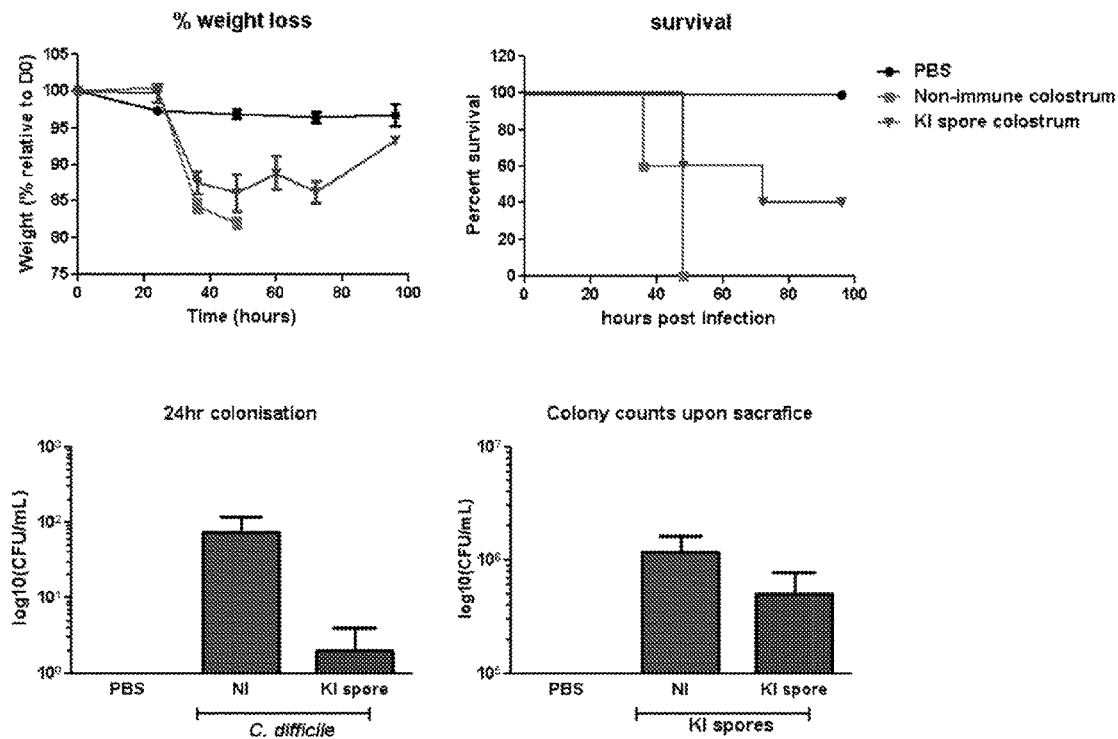

FIG. 11: Administration of antibodies that bind to *C. difficile* endospores is effective for the prevention of *C. difficile* associated weight loss, *C. difficile* associated mortality, *C. difficile* colonisation, and shedding of *C. difficile* spores.

Groups of male, 6-7 week old, C57/BL6 mice were pre-treated with an antibiotic cocktail for 7 days. Mice were administered either non-immune or KI spore colostrum (in the drinking water) for 2 days prior to infection with *C. difficile* KI endospores ($10^3$ spores/mouse). Mice were kept on colostrum during the course of the trial and monitored for weight loss, survival and spore shedding in faeces. N=5 mice/group. Results show hyperimmune colostrum derived from cows vaccinated with endospores from *C. difficile* strain KI comprises antibodies are effective in treating weight loss associated with *C. difficile* infection, and are highly effective in preventing *C. difficile* associated mortality. Results also show hyperimmune colostrum derived from cows vaccinated with endospores from *C. difficile* strain KI comprises antibodies are highly effective at inhibiting *C. difficile* colonisation of mice at 24 hours, and reducing the numbers of *C. difficile* spores in the faeces.

Figure 12:
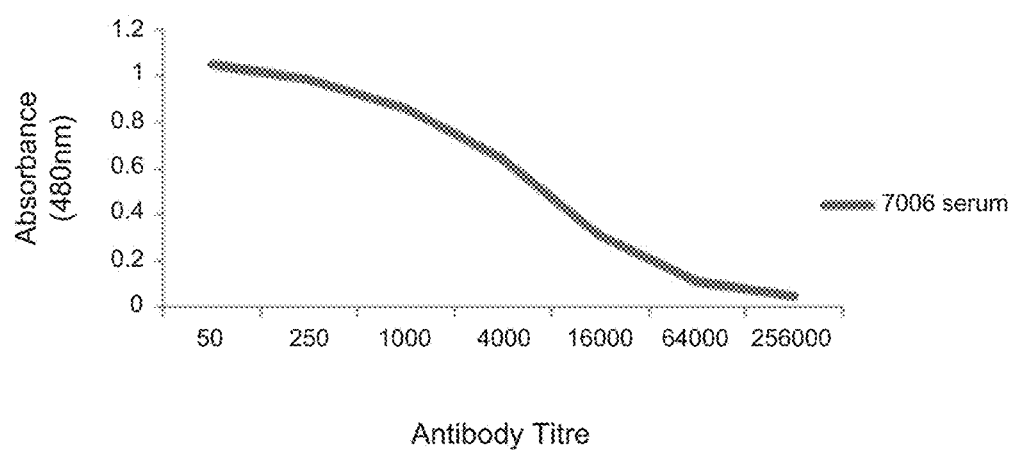

FIG. 12: Detection of antibodies that bind to *C. difficile* vegetative cells in bovine serum.

Results show serum derived from cows vaccinated with *C. difficile* strain KI vegetative cells comprises antibodies that bind to *C. difficile* vegetative cells. The presence of specific anti-vegetative cell antibodies was confirmed by ELISA. Each well was coated with $1\times10^6$ KI cells and incubated with 4-fold serial dilutions (starting from a 1:50 dilution of serum) of #7006 third bleed serum. The antibody titre for this serum was determined to be 64,000.

FIG. 13: Detection of antibodies that bind to *C. difficile* vegetative cells, and demonstration that antibodies that bind to *C. difficile* vegetative cells of a first strain bind to vegetative cells of a second strain.

Results show serum derived from cows vaccinated with *C. difficile* vegetative cells bind to *C. difficile* vegetative cells. Results also show serum derived from cows vaccinated with *C. difficile* vegetative cells bind to *C. difficile* vegetative cells of different *C. difficile* strains. Immunoblotting was first performed in order to detect antibodies directed against vegetative *C. difficile* cells. Whole cell lysates from KI (the strain the antibodies were generated against) as well as other clinically relevant human and animal *C. difficile* isolates were loaded on a 12% SDS-PAGE gel. After transfer to nitrocellulose, the membranes were probed with either the pre-bleed or 3rd bleed (1:10,000) from cow #7006. Antibodies against KI bacterial proteins were detected. Furthermore, the antibodies generated against this hypervirulent strain appeared cross-reactive to a number of different *C. difficile* isolates. Lanes in A and B are as follows: 1. Ladder, 2. KI, 3. JGS6133, 4. AI35, 5. CD71, 6. VPI10463, 7. SP, 8. CD37. CD84, 10. CD39, 11. M322630, 12. M322832, 13. CD63, 14. FW07/06, 15. JIR8078.

Figure 14:
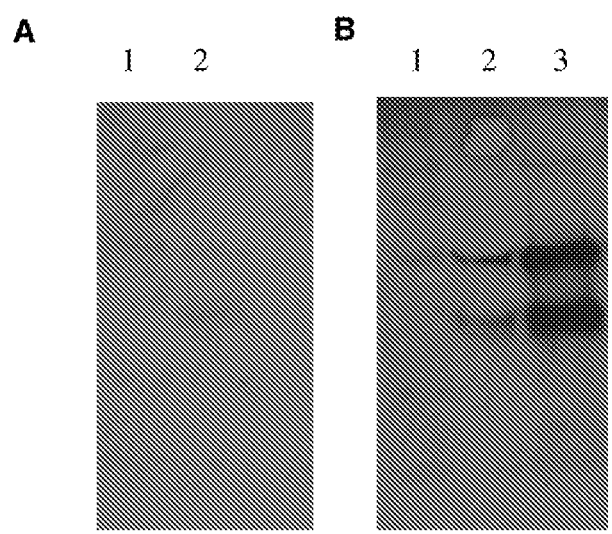

FIG. 14: Detection of antibodies that bind to *C. difficile* S-layer proteins in bovine hyperimmune colostrum.

To identify the dominant protein bands of FIG. 13, two bands of approximately 49 kDa and 35 kDa from KI were excised from a SDS-PAGE gel and sent to APAF for 1D nanoLC ESI MS/MS analysis. These bands were identified as the high molecular weight and low molecular weight components of SlpA, the major protein located on the *C. difficile* S-layer. FIG. 14 shows immunoblots using extracted SlpA from KI (FIG. 14A) to confirm that the antibodies are against S-layer proteins. The identification of these proteins has been confirmed by mass spectrometry of excised bands from an SDS-PAGE gel loaded with S-layer preparations (SLP). Lanes in panel A (Cow #7006, Pre bleed) are as follows; 1. Ladder, 2. SLP from *C. difficile* strain KI. Lanes in panel B (Cow #7006, Third bleed) are as follows; 1. Ladder, 2. blank (contains spill-over from lane 3, and 3. SLP from *C. difficile* strain KI.

FIG. 15: Administration of antibodies that bind to *C. difficile* vegetative cells is effective for the prevention of *C. difficile* associated weight loss and *C. difficile* associated mortality.

Results show hyperimmune colostrum derived from cows vaccinated with vegetative cells from *C. difficile* strain KI comprises antibodies are effective in treating weight loss associated with *C. difficile* infection, and are highly effective in preventing *C. difficile* associated mortality. Groups of male, 6-7 week old, C57/BL6 mice were pre-treated with an antibiotic cocktail for 7 days. Mice were administered either non-immune or #7006 vegetative cell colostrum (in the drinking water) for 2 days prior to infection with *C. difficile* KI endospores ($10^3$ spores/mouse). Mice were kept on colostrum during the course of the trial and monitored for weight loss, survival and vegetative cell/spore shedding. Data below is pooled from two independent mouse trials. N=10 mice/group. Mice that received vegetative cell-specific colostrum showed delayed weight loss and increased survival (40%) compared to mice that received non-immune colostrum. The mice that received non-immune colostrum rapidly lost weight and succumbed to infection by 36 hrs.

Figure 16:
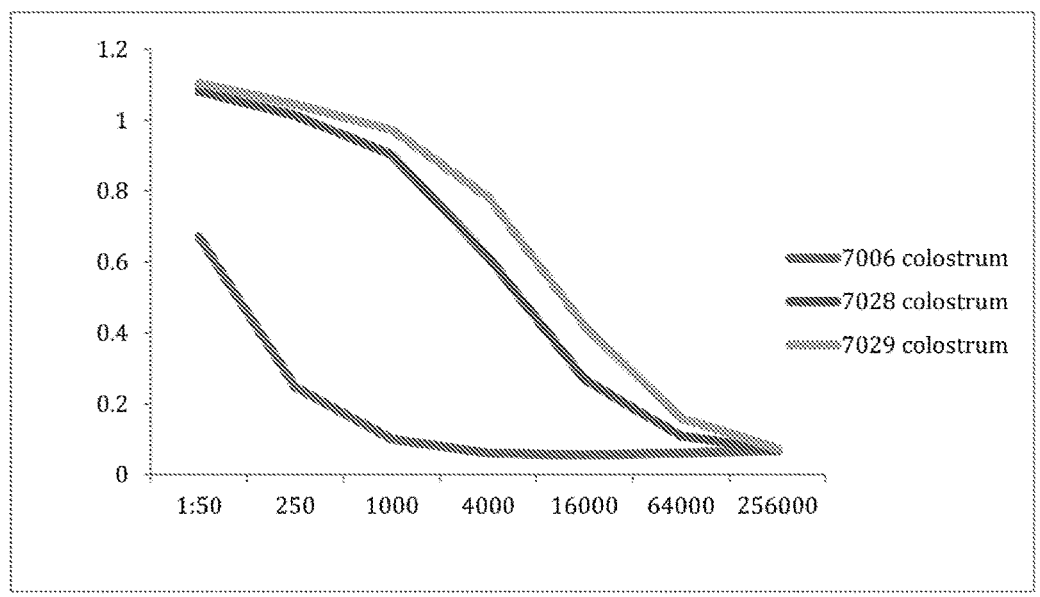

FIG. 16: Detection of antibodies that bind to *C. difficile* vegetative cells in bovine hyperimmune colostrum.

Results show hyperimmune colostrum derived from cows vaccinated with *C. difficile* strain KI vegetative cells comprises antibodies that bind to *C. difficile* vegetative cells. The presence of specific anti-vegetative cell antibodies was confirmed by ELISA. The colostrum antibody titres for cow #7028 and cow #7029 are 16,000-64,000 and 256,000 respectively.

Figure 17:
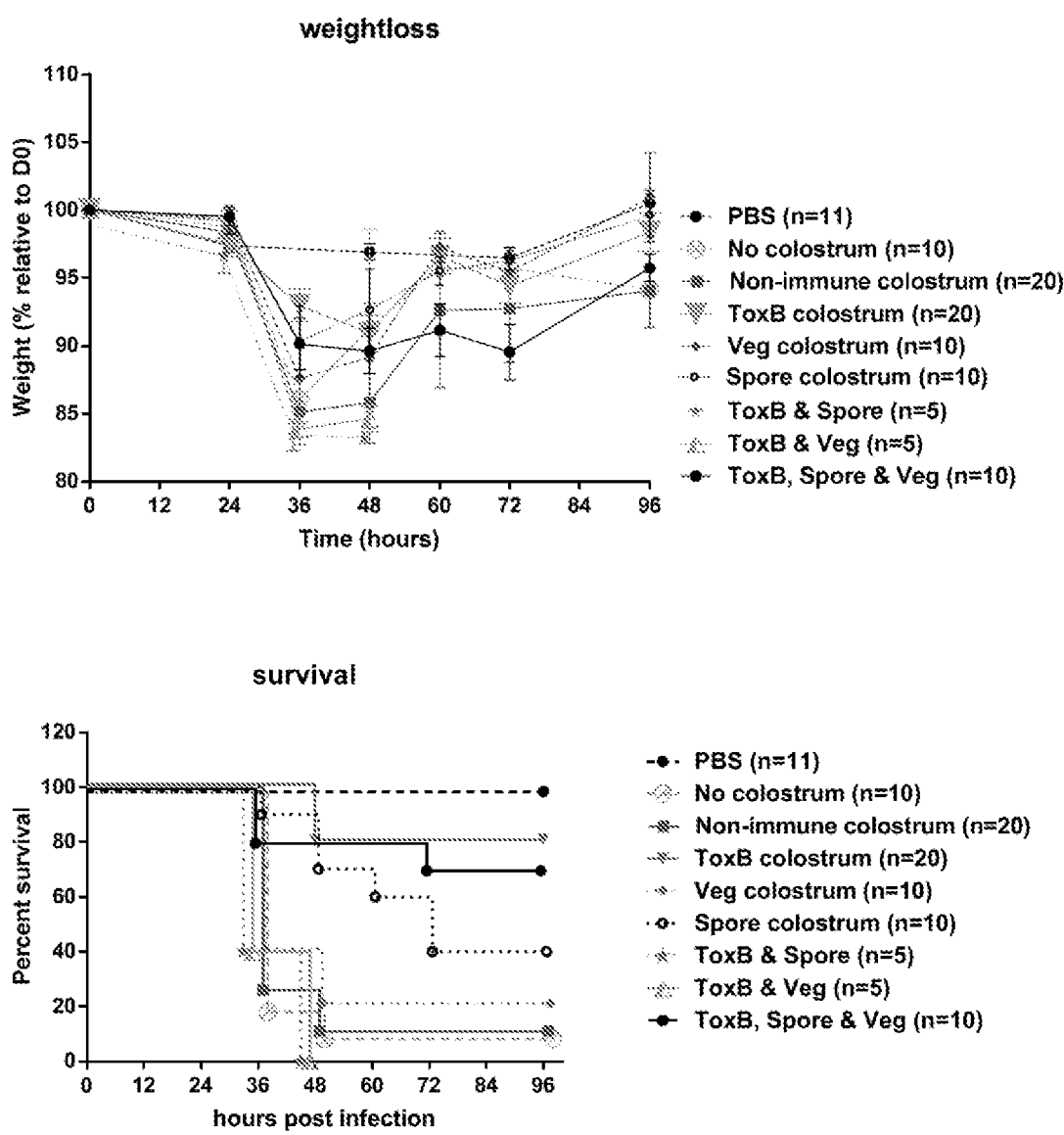

FIG. 17: Administration of combinations of antibodies that bind to *C. difficile* antigens is effective for the prevention of *C. difficile* associated weight loss and *C. difficile* associated mortality.

Results show hyperimmune colostrum derived from cows vaccinated with different antigens derived from *C. difficile* comprises antibodies are effective in treating weight loss associated with *C. difficile* infection, and are highly effective in preventing *C. difficile* associated mortality. Groups of male, 6-7 week old, C57/BL6 mice were pre-treated with an antibiotic cocktail for 7 days. Mice were administered either non-immune, Toxin B colostrum or a combination of Toxin B, spore and vegetative cell colostrum (1:1:1) in the drinking water for 2 days prior to infection with *C. difficile* KI endospores ($10^3$ spores/mouse). Mice were kept on colostrum during the trial and were monitored for weight loss and morbidity. Data is pooled from at least two independent mouse trials. N≥10 mice/group. Results demonstrate uninfected mice (PBS) do not lose weight and survive the duration of the trial. Mice that received no colostrum or non-immune colostrum displayed severe weight loss and mortality. Mice that received vegetative cell colostrum displayed weight loss and 20% survival. Mice that received spore colostrum displayed less weight loss and 40% survival. Mice that received Toxin B colostrum displayed less weight loss and 80% survival. Mice that received vegetative cell and Toxin B colostrum combination (1:1) and spore and Toxin B colostrum combination (1:1) displayed severe weight loss and mortality. Mice that received a combination of vegetative cell, spore and Toxin B colostrum (1:1:1) displayed less weight loss and 70% survival. These results indicate that antibodies that bind to *C. difficile* Toxin B alone or a combination of *C. difficile* antigens in bovine hyperimmune colostrum are effective in neutralising the activity of Toxin B in vivo and other antigens, thereby preventing damage to the gastrointestinal tract of pre-treated mice.

Figure 18:
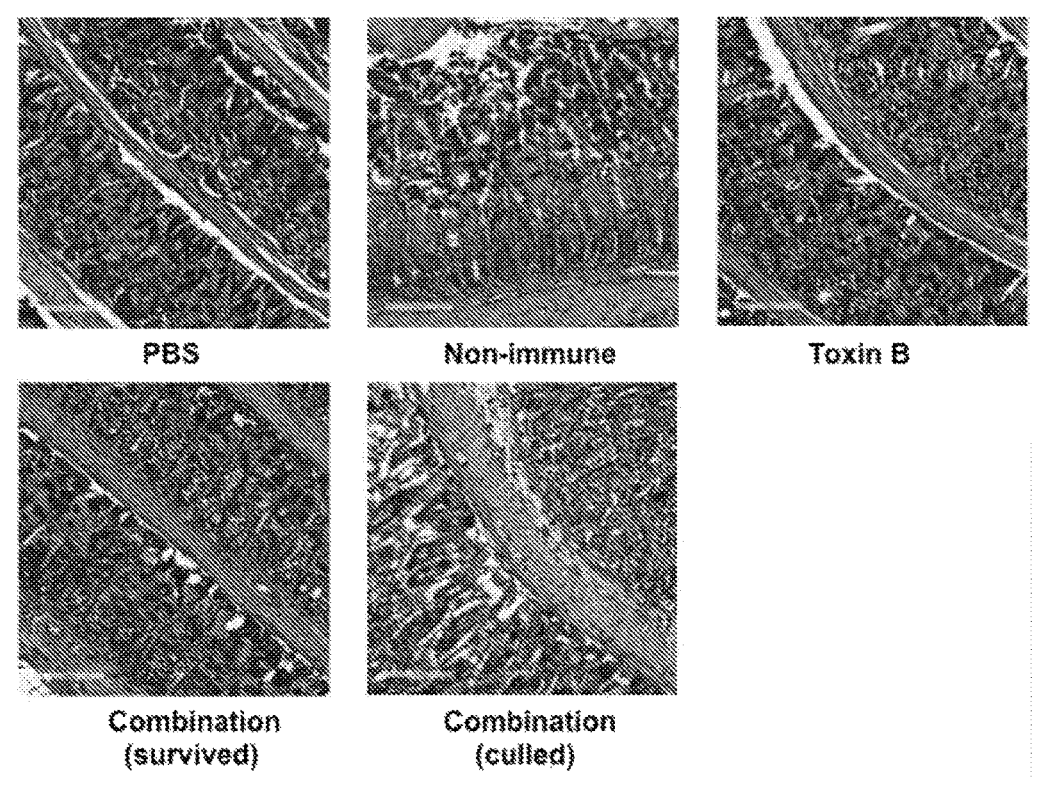

FIG. 18: Administration of antibodies that bind to *C. difficile* Toxin B in bovine hyperimmune colostrum reduces *C. difficile* associated gastrointestinal damage.

Results show hyperimmune colostrum derived from cows vaccinated with Toxin B from *C. difficile* strain 630 comprises antibodies are effective in halting the histopathologic damage associated with *C. difficile* infection. Groups of male, 6-7 week old, C57/BL6 mice were pre-treated with an antibiotic cocktail for 7 days. Mice were then infected with *C. difficile* KI endospores ($10^3$ spores/mouse). 6 hours following infection, mice were administered 200 µl of either non-immune or Toxin B colostrum or 100 µl of vancomycin (6 mg/mL) by oral gavage. Following oral gavage, colostrum (10% w/v) or vancomycin (0.4 mg/mL) was administered fresh daily in the water bottles where the mice could drink ad libitum. Mice were kept on colostrum during the course of the trial and the colon and caecum of mice were collected and analysed for histopathologic damage. Representative images of sections of colonic tissue are shown stained with PAS/alcian blue. Results demonstrate mice given non-immune colostrum displayed severely damaged colonic tissue compared to the mice that were given antibodies that bind to C. difficile Toxin B in bovine hyperimmune colostrum following infection, or the uninfected (PBS) control mice. These results also show that of mice that received a combination of colostrum (Toxin B, vegetative cell and endospore at a ratio of 1:1:1) following infection and survived the infection showed healthier colons, and 70% of treated mice show prevention of damage to the GI tract than those that received the combination and did not survive.

Figure 19:
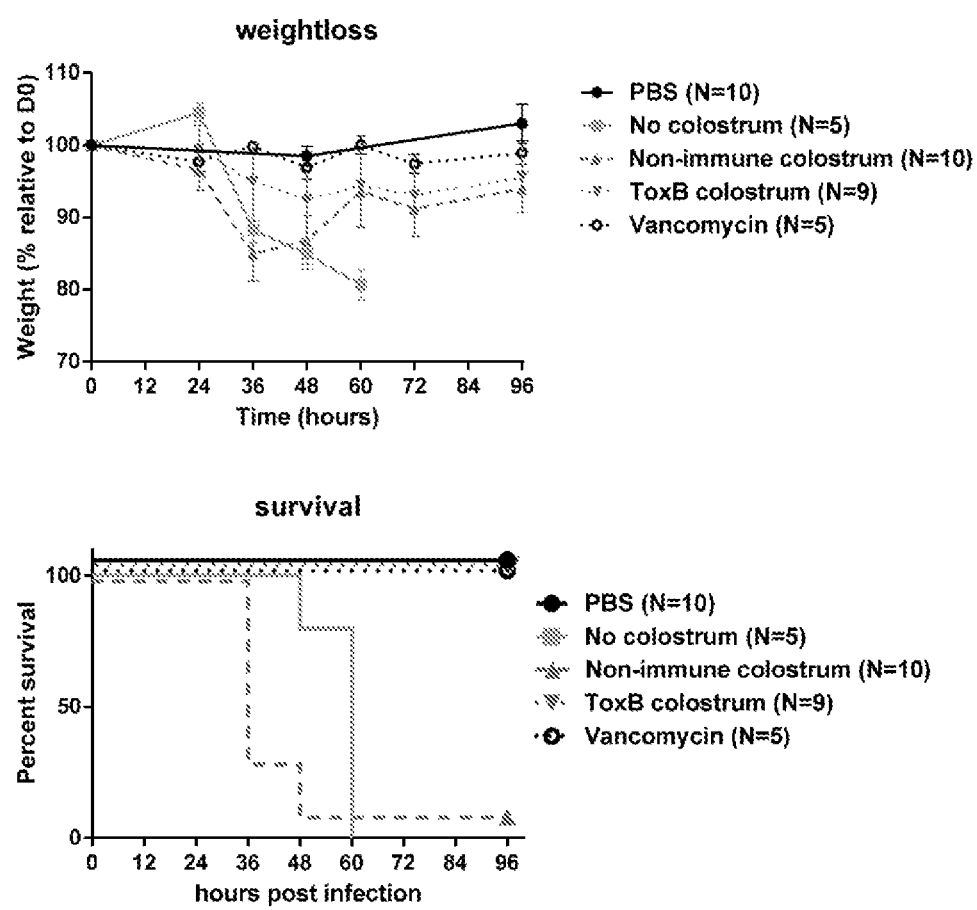

FIG. 19: Administration of antibodies that bind to C. difficile Toxin B are effective for the treatment of C. difficile associated weight loss and C. difficile associated mortality.

Results show hyperimmune colostrum derived from cows vaccinated with recombinant Toxin B derived from C. difficile comprises antibodies that are effective in treating weight loss associated with C. difficile infection, and are highly effective in preventing C. difficile associated mortality. Groups of male, 6-7 week old, C57/BL6 mice were pre-treated with an antibiotic cocktail for 7 days. Mice were infected with C. difficile KI endospores ($10^3$ spores/mouse). 6 hours post infection; mice were given one 200 µl oral gavage of either non-immune colostrum, Toxin B colostrum or 100 ul vancomycin. After oral gavages of specific treatments, mice were given these treatments in drinking water for the duration of the trial and monitored for weight loss and survival. Results demonstrate mice treated with non-immune colostrum displayed severe weight loss and morbidity, as did mice that received no treatment. Mice that were treated with antibodies that bind to C. difficile Toxin B in bovine hyperimmune colostrum post infection displayed less weight loss and marked recovery and thus the results show the Toxin B antibodies therefore halted C. difficile associated mortality. This result was similar to that seen with mice that were treated with the antibiotic control of vancomycin. These results show administration of hyperimmune colostrum derived from cows vaccinated with different antigens derived from C. difficile post infection are effective in treating weight loss associated with C. difficile infection, and are highly effective in preventing C. difficile associated mortality.

DETAILED DESCRIPTION

Previous work characterising virulence factors of C. difficile has focussed on two members of the large clostridial cytotoxin family, known as Toxin A (TcdA) and Toxin B (TcdB), which are considered to be the major virulence factors of C. difficile. Both are potent toxins and cause extensive colonic inflammation and epithelial tissue damage in the infected host. The net effect is rapid fluid loss into the intestinal lumen, which manifests as diarrhoea. In addition to the major toxins, C. difficile may produce a number of other putative virulence factors, including a third toxin known as CDT binary toxin, fimbriae, para-cresol production, the fibronectin binding protein FbpA, the Cwp84 cysteine protease, the putative Cwp66 and CwpV adhesins, and the SlpA S-layer. However, the precise role, if any, that these factors play in the virulence of C. difficile remains to be determined. Recent studies have shown that flagella mutants constructed in strain 630Δerm demonstrated increased adherence to Caco-2 cells, suggesting that flagella do not contribute to epithelial cell adherence. These strains were also more virulent in hamsters in comparison to the wild-type strain, suggesting that flagella are not required for virulence or that repression of motility may be a pathogenic strategy employed by C. difficile in hamsters.

Although the majority of C. difficile strains produce both Toxin A and Toxin B, Toxin A has long been thought to be the major virulence factor for many years on the basis of early studies using purified toxins. In these experiments, hamsters were challenged intragastrically with purified toxin and then monitored for signs of disease. Hamsters succumbed to disease and displayed symptoms typical of C. difficile infection when challenged with purified Toxin A, including fluid accumulation, inflammation and necrosis of intestinal tissues. By contrast, purified Toxin B caused no disease unless the toxin was co-administered with sub-lethal concentrations of Toxin A or if prior intestinal damage was present. This observation led to the suggestion that the toxins might work synergistically, with Toxin B eliciting an effect only after Toxin A had caused prior tissue damage.

Further evidence that Toxin A was the major virulence factor in C. difficile arose from the observation that purified Toxin A alone caused haemorrhage and increased intestinal permeability resulting in severe epithelial cell necrosis in rabbit ileal loops, whereas Toxin B alone showed little enterotoxicity. Vaccination with Toxin A-specific toxoids also fully protected animals against infection with toxigenic strains of C. difficile. Furthermore, it has been observed that a strong humoral response against Toxin A is an important indicator of disease severity in patients infected with C. difficile. In combination, these studies implied that Toxin A was the major toxin responsible for disease resulting from CDI.

More recent work has suggested that Toxin B plays a much more important role than previously anticipated. In light of the Toxin A work discussed above, the identification of clinical strains of C. difficile that do not produce Toxin A but still cause symptomatic disease was perplexing. Experiments using purified toxins clearly indicated that Toxin A was the major mediator of CDI, yet the occurrence of Toxin A-negative, Toxin B-positive isolates suggested otherwise. Additionally, isolation of these strains from diseased patients indicated that Toxin A was not required for Toxin B functional activity in vivo. At a clinical level, the variant strains of C. difficile were indistinguishable from strains producing both toxins because patients infected with Toxin A-negative, Toxin B-positive strains exhibited the full spectrum of symptoms associated with CDI. These studies also suggest that these isolates are associated with more severe disease. The reasons for this are not known; however, the variant Toxin B with altered substrate specificity produced by most Toxin A-negative, Toxin B-positive strains could play a role. Alternatively, the absence of a Toxin A-specific immune response, which is a key determinant in controlling CDAD might contribute to increased disease severity.

Experiments examining the effect of purified toxins on mice carrying human intestinal explants also showed that Toxin B alone could cause all of the symptoms of CDI, even in the absence of Toxin A. In this study, purified Toxin B was shown to be a more potent enterotoxin than Toxin A, causing severe damage to the intestinal epithelium and leading to an acute inflammatory response. These experiments re-established the importance of Toxin B in CDI and challenged the then generally accepted hypothesis that Toxin A was the major C. difficile virulence factor. Research utilising the zebrafish embryo intoxication model subsequently showed that fish treated with purified Toxin B exhibited cardiovascular damage, with a 90% reduction in systemic blood flow and a 20% drop in heart rate, suggesting that Toxin B is cardiotoxic. Therefore, these studies suggest that Toxin B might also have the capacity to cause systemic damage to the host in addition to localised damage within the gut. In this context, it could be of relevance that in a small percentage of patients, infection with *C. difficile* results in multiple organ dysfunction syndrome, possibly as a result of systemic toxin damage.

Despite the detailed studies performed using purified toxins, the individual contribution of Toxin A and Toxin B to disease remained ambiguous primarily because the research findings did not correlate with the variant clinical isolates that were becoming increasingly common.

Work of one of the present inventors using *C. difficile* tcdA and tcdB toxin mutants has implicated Toxin B as the major virulence factor of *C. difficile*, not Toxin A, and suggested Toxin B does not require the presence of Toxin A to cause disease. This finding was consistent with correlates with the clinical situation and the isolation of naturally occurring Toxin A-negative, Toxin B-positive isolates, which are fully virulent, as discussed above. In particular, in these experiments (Lyras et al. Nature 458, 1176-1179 (30 Apr. 2009)), groups of Syrian golden hamsters were infected with either the wild-type strain or one of the independently derived toxin mutants. When infected with the wild-type strain, 90% of hamsters succumbed to disease and died. Similarly, when infected with the mutants that no longer produced Toxin A, approximately 94% of hamsters died, providing clear evidence that Toxin A was not needed for disease. By contrast, when hamsters were infected with mutants that no longer produced Toxin B, only 22% succumbed to infection, and subsequent analysis of these hamsters revealed that the faecal pellets contained Toxin B, suggesting that in these animals reversion of the mutants to wild type had occurred.

However, more recent work has re-established the importance of both Toxin A and Toxin B (Kuehne et al. Nature 467, 711-713 (7 Oct. 2010)). In this work using gene knockouts to inactivate the toxin genes permanently, it was demonstrated that *C. difficile* producing either one or both toxins showed cytotoxic activity in vitro that translated directly into virulence in vivo. Furthermore, by constructing the first ever double-mutant strain of *C. difficile*, in which both toxin genes were inactivated, virulence was completely attenuated.

Accordingly, this work makes it clear that effective countermeasures against *C. difficile* should target both toxins, since the presence of either toxin is sufficient for *C. difficile* morbidity and mortality. For example, the data of Kuehne et al. suggests that countermeasures against *C. difficile* targeting Toxin B alone would not diminish cytotoxicity in vitro, or colonisation or mortality in vivo, in the absence of targeting Toxin A.

In direct contrast to the aforementioned findings, the present inventors have demonstrated that antibodies that bind to Toxin B are able to inhibit *C. difficile* associated disease. In particular, the present invention is based in part on the finding that antibodies that bind to *C. difficile* Toxin B, a *C. difficile* vegetative cell antigen or a *C. difficile* endospore antigen are capable of inhibiting *C. difficile* associated morbidity, *C. difficile* associated mortality, and faecal shedding of *C. difficile* spores from infected individuals.

The present inventors have established a model of *C. difficile* associated disease (Examples 1 to 3). FIG. 1 demonstrates that oral infection of mice with *C. difficile* spores results in *C. difficile* associated disease, as measured by weight loss following infection. FIG. 2 demonstrates colonisation with and faecal shedding of *C. difficile* following infection. FIG. 3 demonstrates *C. difficile* infection results in *C. difficile* associated damage to the caecum and colon, as measured by histopathologic change following infection.

Importantly, the present inventors have demonstrated hyperimmune colostrum derived from cows vaccinated with Toxin B from *C. difficile* strain 630 comprises antibodies that bind to Toxin B (Example 4 and FIG. 4), and that hyperimmune colostrum derived from cows vaccinated with Toxin B from *C. difficile* strain 630 comprises antibodies that bind to Toxin B from other strains, including purified historical Toxin B (Toxin B-Hist) and hypervirulent strain 027 Toxin B (Toxin B-HV), but not Toxin A (FIG. 4B). Accordingly, the methods and compositions of the present invention are expected to be effective for the treatment and/or prophylaxis of *C. difficile* associated disease caused by different *C. difficile* strains. For example, FIG. 4 demonstrates hyperimmune colostrum derived from cows vaccinated with Toxin B from *C. difficile* strain 630 comprises antibodies that bind to Toxin B from strains K1, M7404, VPI10463, CD196, R20291, 'CA' and JGS6133 strains of *C. difficile*.

Accordingly, in a first aspect, the present invention provides a composition comprising mammalian or avian antibodies for use in the treatment and/or prophylaxis of at least one symptom of *Clostridium difficile* associated disease, wherein the antibodies comprise: a) antibodies that bind to a *Clostridium difficile* Toxin B; and b) antibodies that bind to at least one *Clostridium difficile* vegetative cell antigen, and/or antibodies that bind to at least one *Clostridium difficile* endospore antigen.

As used herein, the terms "antibody", "antibodies" and the like include any monospecific or bispecific molecule comprising a portion of the light chain variable region and/or the heavy chain variable region to effect binding to the epitope to which the antibody has binding specificity. It will be understood that if the immune material is raised by vaccination of mammals or avians it will contain polyclonal antibodies. Antibodies, as used herein, may also include polyclonal, humanized, anti-idiotypic, chimeric or single chain antibodies. Exemplary antibodies and fragments thereof that may be prepared according to this aspect of the invention include intact immunoglobulin molecules, substantially intact immunoglobulin molecules and fragments that contain a paratope.

Fragments, as used herein, typically include a portion of an antibody molecule that retains the ability to specifically bind to an antigen (e.g., an influenza antigen) and include, but are not limited to, Fab, Fab', F(ab')2 and F(v). Antibody fragments may be obtained from antibodies such as described above by methods such as digestion by enzymes, such as pepsin or papain and/or by cleavage of the disulfide bridges by chemical reduction. Single chain antibodies are also intended to be encompassed within the term "fragment". Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) Proc. Natl. Acad. Sci. USA 90:6444-6448; Poljak, R. J., et al. (1994) Structure 2:1121-1123). Still further, an antibody or fragment thereof may be part of a larger immunoadhesion molecule, formed by covalent or non-covalent association of the antibody or fragment thereof with one or more other proteins or peptides. Examples of such immunoadhesion molecules include use of the streptavidin core region to make a tetrameric scFv molecule (Kipriyanov, S. M., et al. (1995) Human Antibodies and Hybridomas 6:93-101) and use of a cysteine residue, a marker peptide and a C-terminal polyhistidine tag to make bivalent and biotinylated scFv molecules (Kipriyanov, S. M., et al. (1994) Mol. Immunol. 31:1047-1058).

As used herein, "treatment" refers to the reduction or elimination of the severity of a symptom of the disease, the frequency with which such a symptom is exhibited, or both. The term includes an action that occurs while a patient is suffering from a *C. difficile* infection or associated disorder that reduces the severity of one or more symptoms or effects of a *C. difficile* infection or *C. difficile* associated disease or symptom.

As used herein, "prophylaxis" refers to completely or partially preventing or inhibiting a symptom of the disease or the frequency with which such a symptom is exhibited, or a reduction of the risk of acquiring a given symptom, of CDAD. Prophylaxis includes inhibiting *C. difficile* associated diarrhea, preventing *Clostridium difficile*-associated diarrhea, decreasing the severity of *Clostridium difficile*-associated diarrhea or improving signs and symptoms related to having *Clostridium difficile*-associated diarrhea. Prophylaxis includes inhibiting, preventing, or decreasing the severity a symptom of CDAD as described herein. The term includes action that occurs before a patient begins to suffer from *C. difficile* infection or associated disorder, such as but not limited to bowel or gastrointestinal disorder, that delays the onset of, and/or inhibits or reduces the severity of a *C. difficile* infection or *C. difficile* associated disease or symptom.

As used herein, "*C. difficile*-associated disease" refers to any disease involving unwanted growth, toxin production, or tissue invasion in the bowel by *C. difficile*. *C. difficile*-associated diseases are well known and specifically include antibiotic-associated diarrhoea (also known as *C. difficile* colitis), pseudomembranous colitis, and *C. difficile*-associated toxic megacolon. *C. difficile* colitis generally refers to profuse, watery diarrheal illness associated with the presence of at least one *C. difficile* toxin. Pseudomembranous colitis refers to a severe form of *C. difficile* colitis further characterized by bloody diarrhoea, fever, and bowel wall invasion by *C. difficile*. The appearance of "pseudomembranes" on the surface of the colon or rectum may be diagnostic of the condition. The pseudomembranes are composed principally of inflammatory debris and white blood cells. The term also includes a relapse of *C. difficile* infection in a subject who has suffered from *C. difficile* infection or *C. difficile*-associated disease previously.

As used herein, a "symptom" of *C. difficile*-associated disease includes infection with *C. difficile*, or a symptom of *C. difficile* associated disease such as mild self-limiting diarrhoea, diarrhoea, abdomen pain, fever and loss of appetite, abdominal pain, to life-threatening conditions such as pseudomembranous colitis and cytotoxic megacolon or other clinical symptoms associated with *C. difficile* associated disease, including those described herein.

Other symptoms of *C. difficile*-associated disease include colonisation with *C. difficile* bacteria, weight loss, cytotoxicity, gastrointestinal damage, histopathologic change in the gastrointestinal tract, shedding of *C. difficile* in the faeces and mortality.

Histopathologic change is change in a tissue during *C. difficile* infection or CDAD that may be detected using histological methods well known in the field. In one embodiment the histopathologic change is change in the gastrointestinal tract. In another embodiment the histopathologic change is change in a tissue other than a tissue of the gastrointestinal tract.

*C. difficile* is shed in the faeces of infected individuals. Reducing *C. difficile* shedding includes decreasing the number of *C. difficile* spores in the faeces of an infected individual.

In another embodiment, the at least one symptom of *Clostridium difficile* associated disease is selected from the group consisting of diarrhea, abdominal pain, fever, loss of appetite, pseudomembranous colitis, cytotoxic megacolon, *C. difficile* colonisation, weight loss, cytotoxicity, gastrointestinal damage, histopathologic change in the gastrointestinal tract, faecal shedding of *C. difficile* spores, and *C. difficile* associated mortality.

As used herein, "Toxin B" refers to a family of protein cytotoxins of approximately 270 kDa in size which are similar to Toxin A, but significantly more cytotoxic. Like Toxin A, Toxin B has an enzyme activity within the N-terminal region which acts to disrupt the cytoskeleton of the mammalian cell causing cell death. As will be described below, there are a number of naturally occurring variants of Toxin B within the strains of *C. difficile* which are called 'toxinotypes'.

Toxins A and B are both members of the large clostridial toxin (LCT) family, which includes the lethal and haemorrhagic toxins (TcsL and TcsH, respectively) of *Clostridium sordellii*, alpha toxin (TcnA) from *Clostridium novyi* and TpeL from *Clostridium perfringens* isolates from domestic livestock. The LCTs are an important family of bacterial toxins; they are monoglycosyltransferases that inactivate Rho family GTPases, including Rho, Rac, Ras, Ral and Cdc42, through the covalent transfer of a glucose moiety or, for TcnA and TpeL, an N-acetylglucosamine moiety. Glycosylation of these proteins locks them into an inactive conformation thereby blocking downstream cellular activities that require functional Rho GTPases.

Without wishing to be bound by theory, cellular intoxication is likely to begin with binding of the LCT C-terminus to one or more receptors present on the target cell surface. It is important to note that the exact nature of the toxin receptors is not known at present, with carbohydrate, glycolipid and protein receptors all having been suggested. Following receptor binding, the toxins are endocytosed via clathrin- and dynamin-dependent pathways, before trafficking to the early endosomes of the host cell. Acidification of the endosome is thought to be required for translocation of the toxins into the host cell cytosol. Evidence for this comes from the observation that Toxin B-mediated cytotoxicity can be inhibited by bafilomycin A1, a potent inhibitor of the endosomal vacuolar ATPase pump, which blocks endosomal acidification. Within the endosome, each toxin undergoes a pH-induced conformational change, most probably between the C-terminal CROPs region and the cysteine protease domain, with a protrusion, thought to be involved in membrane insertion or early membrane interaction, appearing to form. Both Toxins A and B can form pores at low pH, with Toxin A-induced pore formation being dependent on the presence of cholesterol. In the case of Toxin B, pore-forming activity is located within the hydrophobic region, more specifically between residues 830 and 990, with glutamate 970 and glutamate 976 being particularly important because they act as pH sensors for membrane insertion. Following pore formation, binding of inositol hexakisphosphate then leads to a conformational change within the cysteine protease domain of the toxin, resulting in autocatalytic cleavage at a site located between the glucosyltransferase and the cysteine protease domains of the protein, with the subsequent release of the active N-terminal glycosyltransferase domain into the cytosol. Rho GTPases are central to many cellular processes such as the organisation of the actin cytoskeleton; they also play a role in controlling epithelial barrier function and are involved in the signalling and motility of immune cells. Inactivation of Rho GTPases by Toxin A or Toxin B therefore has a profound effect on the cell. One of the most striking and early effects of intoxication is the loss of structural integrity of the target cell as a consequence of a decline in the amount of F-actin, resulting from dysregulation of actin depolymerisation. Loss of structural integrity and 'cell rounding' normally precedes apoptosis and finally death of the intoxicated cell, which is thought to occur via a caspase-3 and caspase-9 dependent pathway. Toxin-mediated disruption of the actin cytoskeleton and the subsequent death of colonocytes leads to a loss of intestinal epithelial barrier function and the impairment of cellular tight junctions. Intestinal epithelial cells also release a number of cytokines in response to toxin exposure and these lead to the activation of neutrophils, mast cells, enteric nerves and sensory neurons within the intestinal lamina propria. These in turn release neuropeptides and proinflammatory cytokines resulting in a profound inflammatory response, which further compromises the epithelial barrier function. The loss of epithelial barrier function results in increased intestinal permeability and fluid accumulation, followed by the onset of diarrhoea, which is one of the characteristic features of CDAD.

An antibody is said to "bind to" a certain antigen if it is capable of specifically reacting with the antigen, which for example, may include Toxin B, an endospore antigen or a vegetative cell antigen, to thereby bind the antigen molecule to the antibody. An antibody that binds to an antigen of interest is one capable of binding that antigen with sufficient affinity such that the antibody is useful as a therapeutic agent.

In one embodiment an antibody that "binds to" an antigen is one that binds to an antigen of *C. difficile* with an affinity ($K_a$) of at least $10^4$ M.

As used herein, "vegetative cell" or "vegetative state" refers to the growth stage of a *C. difficile* bacterium or bacteria e.g. the actively growing and dividing stage of *C. difficile*.

As used herein, "spore" refers to both the conventionally used terms "spore" and "endospore". Bacterial endospores are highly resistant to hostile physical and chemical conditions, proving to be one of the most durable types of cells found in nature. They can survive high heat, drying, radiation, and many damaging chemicals and are a dormant form of the bacterium that allows it to survive sub-optimal environmental conditions. Endospores can survive for a very long time and then return to a growing state, a process termed germination. Because endospores are resistant to heat, radiation, disinfectants, and desiccation, they are difficult to eliminate from medical and pharmaceutical materials and are a frequent cause of contamination. "Spore" refers to both the conventionally used terms "spore" and "endospore".

An "antigen" is a molecule or a portion of a molecule capable of being bound by an antibody, which is additionally capable of inducing an animal to produce antibody capable of binding to an epitope of that antigen. An antigen may have one or more than one epitope. The term "epitope" is meant to refer to that portion of any molecule capable of being bound by an antibody that can also be recognized by that antibody. Epitopes or "antigenic determinants" usually consist of chemically active surface groupings of molecules such as amino acids or sugar side chains, and have specific three-dimensional structural characteristics as well as specific charge characteristics.

Accordingly, a vegetative cell antigen is a molecule or a portion of a molecule capable of being bound by an antibody that is present in *C. difficile* vegetative cells.

An endospore antigen is a molecule or a portion of a molecule capable of being bound by an antibody that is present in *C. difficile* endospores.

*C. difficile* endospores, are encased in a multilayered protein structure formed by the ordered assembly of many polypeptides. The endospore contains four protective layers, the core, the cortex, the coat, and the exosporium. The outermost layer of the spore is the exosporium, a thin covering made of protein. Interior to this is the spore coat which is made up of highly cross-linked keratin and layers of spore-specific proteins. The spore coat is impermeable to many toxic molecules and may also contain enzymes that are involved in germination. The cortex lies beneath the spore coat and consists of peptidoglycan. The core wall lies beneath the cortex and surrounds the protoplast or core of the endospore. The core has normal cell structures, such as DNA and ribosomes, but is metabolically inactive.

Some embodiments of the present invention therefore include antibodies that bind to a spore-specific protein, such as, for example, an exosporium protein, a spore coat protein, a spore cortex protein, a spore inner membrane protein, or a spore core protein of *C. difficile*. Spore coat assembly proteins include CotA, CotB, CotC, CotD, CotE and SodA. The exosporium is a loose-fitting sac-like structure enveloping the mature spore. Some embodiments of the present invention therefore include antibodies that bind to an exosporium-specific protein. Exosporium proteins include BclA1, BclA2 and BclA3.

In one embodiment, the antibodies are polyclonal antibodies.

Antibodies of the present invention may be a polyclonal antibody. As used herein, the term "polyclonal antibody" refers to an antibody produced from more than a single clone of plasma cells. In contrast "monoclonal antibody" refers to an antibody produced from a single clone of plasma cells. The preparation of polyclonal antibodies is well known. A polyclonal antibody to a target antigen may be obtained by immunizing any of a variety of host animals with an immunogen. Any of a wide variety of immunization protocols may be used. The host animal may be any mammal, for example, a mouse, hamster, rat, rabbit, guinea pig, goat, sheep, horse, cow, buffalo, bison, camel, or llama. A host animal may be a bird, for example, a chicken or a turkey. In some embodiments, an antibody preparation, rather than obtained from a blood sample, is obtained from another fluid source, for example, from milk, colostrums, egg white, or egg yolk. In some embodiments, an antibody preparation is obtained, not by immunizing a host animal with the target antigen, but rather, from an individual with a prior exposure to the antigen or from pooled serum, for example, from pooled human serum.

The hyperimmune colostrum of the present invention that comprises antibodies that bind an antigen is raised against a vaccine comprising a *Clostridium difficile* antigen.

In one embodiment, the antigen vaccine used to generate the antibodies of the present invention is a *C. difficile* toxin or a fragment thereof, which has optionally been purified. Suitable *C. difficile* toxins include any *C. difficile* toxins that cause or are associated with CDAD or a symptom thereof. In a further embodiment, the toxin is *C. difficile* Toxin B or a fragment thereof. The *C. difficile* toxin may also be a toxin selected from one of the toxinotypes 0 to XV as defined hereinbefore.

The *C. difficile* Toxin B may be purified or a recombinant *C. difficile* Toxin B.

Production of purified *C. difficile* Toxin B is exemplified in the Examples. In certain embodiments, the immunogen is a *C. difficile* toxin variant.

The vaccines used in the present include recombinant Toxin B from strain 630, Toxin B purified from strain KI, and Toxin B purified from strain AI35.

Production of *C. difficile* endospores and *C. difficile* vegetative cells is exemplified in the Examples.

The vaccines used in the present include strain KI endospores, strain KI vegetative cells, and strain KI S-layer preparations The immunogen used to generate the antibodies of the present invention may also be partially or completely inactivated, i.e. have reduced toxicity. Examples of modification include: chemical treatment (e.g. treatment with UDP-dialdehyde, formaldehyde, formalin, glutaraldehyde, peroxide, or oxygen) and recombinant methods (e.g. deletions or mutations in the toxin). For example, the immunogen may be a *C. difficile* toxoid or a fragment thereof derived from the native toxin by treatment with formaldehyde. Alternatively, a recombinant toxoid may be generated by selectively inactivating the active site motif by site-directed mutagenesis. An example of site directed mutagenesis to reduce or ablate the toxin effects of Toxins A and B is modification of the DXD motif in the N-terminal domain of the toxin. The aspartates and/or other residues may be mutated to e.g. alanine in order to reduce the biological activity of either Toxin A and B.

Antigens may be formulated with an adjuvant. Suitable adjuvants may include alum (aluminium phosphate or aluminium hydroxide), which is used widely in humans, and other adjuvants such as saponin and its purified component Quil A, Freund's complete adjuvant, RIBBI adjuvant, and other adjuvants used in research and veterinary applications.

The present inventors have demonstrated antibodies that bind to 'standard' Toxin B (TcdB-$_{HIST}$) from historical strain 630, and antibodies that bind to 'hypervirulent' Toxin B (TcdB$_{HV}$) from strain R2029. The present inventors have also demonstrated hyperimmune colostrum derived from cows vaccinated with Toxin B from *C. difficile* strain 630 comprises antibodies that bind to Toxin B from strains KI, M7404, VPI10463, CD196, R20291, 'CA' and JGS6133 strains of *C. difficile*. Furthermore, the present inventors have demonstrated hyperimmune colostrum derived from cows vaccinated with vegetative cells from *C. difficile* strain KI comprises antibodies that bind to vegetative cells from *C. difficile*, and that hyperimmune colostrum derived from cows vaccinated with vegetative cells from *C. difficile* strain KI comprises antibodies that bind to vegetative cells from *C. difficile* from other strains (FIG. 13). For example, the present inventors have demonstrated that hyperimmune colostrum derived from cows vaccinated with vegetative cells from *C. difficile* strain KI comprises antibodies that bind to vegetative cells from *C. difficile* from strains KI, 8374, AI35, CD71, VPI10463, SP, CD37, CD84, CD39, M322832 and JIR8078.

A "strain" of *C. difficile* is a sample of *C. difficile* bacteria taken from an infected individual on a unique occasion. Routine methods may be used to distinguish between different *C. difficile* strains.

In one embodiment, the *C. difficile* strain is a strain described herein. The strains used in the present invention include strains selected from the group consisting of KI, 630, R20291, M7404, VPI10463, CD196, R20291, 'CA', JGS6133, AI35, CD71, VPI10463, SP, CD37, CD84, CD39, M322832, JIR8078, M322630, CD63, FW07/06, and JIR8078.

In one embodiment, the *C. difficile* strain used to prepare an antigen vaccine is selected from one of toxinotypes 0 to XV. Preferred toxinotypes (including example Ribotypes and Strains) are listed in Table 1 below.

TABLE 1

Preferred *C. difficile* toxinotypes.

| Toxinotype | Example Ribotypes | Example Strains |
|---|---|---|
| 0 | 001, 106 | VPI10463 |
| I | 003, 012, 102 | EX623 |
| II | 103 | AC008 |
| III | 027, 034, 075, 080 | R20291, QCD-32g58 |
| IV | 023, 034, 075, 080 | 44767 |
| V | 066, 078 | SE881 |
| VI | 045, 063, 066 | 51377 |
| VII | 063 | 57267 |
| VIII | 017, 047 | 1470 |
| IX | 019 | 51680 |
| X | 036 | 8864 |
| XI | 033 | 1S58, R11402 |
| XII | 056 | IS25 |
| XIII | 070 | R9367 |
| XIV | 111 | R10870 |
| XV | 122 | R9385 |

Recently, morbidity and mortality resulting from GOAD have increased significantly, most probably as a result of changes in the virulence of the causative strains coupled with changes in antibiotic usage patterns. Hypervirulent strains, belonging predominantly to the BI/NAP1/027 group, appear to cause epidemics more readily than other *C. difficile* strains, leading to an increased incidence of CDI and greater disease severity. Infections by these strains are conservatively estimated to cost the USA healthcare system $3.2 billion per year. Notably, these isolates are resistant to fluoroquinolones, produce significantly more TcdA and TcdB and often produce more spores in comparison to historical strains. Genotypic and phenotypic comparison of the hypervirulent BI/NAP1/027 isolates with historical strains has identified a number of differences that might contribute to the increased virulence of these strains. Of particular interest is the observation that these strains have a nonsense mutation in tcdC, which is postulated to be responsible for the increased levels of toxin produced by these strains. Recent work using a tcdC-complemented derivative of a BI/NAP1/027 strain has confirmed this hypothesis and has shown that this naturally occurring mutation is an important factor in increased toxin production from these strains and in the development of a more virulent phenotype. BI/NAP1/027 isolates also encode a variant form of TcdB, which was recently shown to be cytotoxic to a wider range of cell lines in comparison to TcdB from historical isolates.

*C. difficile* is a genetically heterogeneous species with substantial chromosomal variation between strains. This genetic variation extends to the PaLoc region, including the toxin structural genes tcdA and tcdB, facilitating the development of a *C. difficile* toxinotyping scheme. This typing scheme classifies strains, based on defined PCR analysis and subsequent restriction endonuclease analysis of DNA fragments, into 'toxinotypes', reflecting specific nucleotide changes that are present within the PaLoc. There are currently over 30 toxinotypes in addition to toxinotype 0, of which strain VPI10463 is the archetypal member, serving as a reference strain for the scheme. Although the impact of variant toxinotypes on disease is not known, it is clear that mutations within the PaLoc can have a profound effect on the toxins produced by a particular strain. In the most striking cases, these mutations can abolish the production of one or both of the major toxins, as seen in the Toxin A-negative, Toxin B-positive variant strains, the majority of which are toxinotype VIII, X, XXX and XXXI, or in Toxin A-negative, Toxin B-negative isolates such as toxinotype XIa and XIb. Note that the latter group of strains, lacking both LCTs, do not cause disease and are considered avirulent. Recently, an extensive survey of genetic variation within the PaLoc of a large number of UK isolates (n=1290) was carried out in conjunction with multilocus sequence typing (MLST) analysis. Evidence for the acquisition of the PaLoc by genetic recombination was obtained from the analysis of PCR ribotype 078 strains within one of the five major *C. difficile* clades, but in general the results showed that genetic variation in the PaLoc was more likely to arise by mutation.

Without wishing to be bound by theory, it might be of clinical relevance that variant toxins have also been found to have alterations in their substrate specificity, which could have an impact on disease severity and outcome. Isolates belonging to toxinotypes VIII, X and XIV, for example, produce Toxin B proteins that inactivate an altered subset of Rho family GTPases in comparison to Toxin B from reference strains. Specifically, Toxin B from the reference strain VPI10463 glucosylates Rho, Rac and Cdc42, whereas the equivalent toxin produced by toxinotype VIII and X strains glucosylates Rap, Ral and R-Ras but no longer modifies Rho. Interestingly, in the mouse disease model, purified Toxin B produced by the toxinotype X strain 8864 was more toxic than that from strain VPI10463 with a lethal dose approximately eightfold lower than the toxinotype 0-specific toxin.

Toxin B produced by epidemic BI/NAPI/027 *C. difficile* strains is also a variant toxin. Recently, the properties of the 'hypervirulent' Toxin B (TcdBHV) from strain R20291 were compared with the 'standard' toxin (TcdBHIST) from historical strain 630. Although these two toxins were found to have 92% identity overall, much more variation was identified in the C-terminal receptor binding domain with some regions showing as little as 80% identity. Furthermore, functional comparison of purified Toxin B from strain VPI10463 (which is identical to that from strain 630 and is also defined as TcdBHIST) and a BI/NAPI/027 strain showed that TcdBHV was able to enter cells much more rapidly than TcdBHIST, resulting in more extensive tissue destruction and necrosis in the zebrafish embryo intoxication model. It is possible that differences in the receptor binding domain of TcdBHV could facilitate binding of the toxin to a more widely distributed host receptor not recognised by TcdBHIST or that these differences could enable the toxin to bind to multiple different receptors in different tissues that TcdBHIST would not normally bind. Regardless of the underlying explanation, it is highly probable that the TcdBHV variations play an important role in the hypervirulence of BI/NAPI/027 strains. Note that in addition to the well characterised toxin variations described above, other variant toxins that differ in size, substrate specificity and antigenicity have been identified; however, the clinical significance of these toxins is not known.

As discussed above, the present inventors have demonstrated that antibodies that bind to a *Clostridium difficile* Toxin B further bind to a *Clostridium difficile* Toxin B of a different toxinotype to the Toxin B toxinotype of the vaccine. Importantly, the present inventors have demonstrated hyperimmune colostrum derived from cows vaccinated with Toxin B from *C. difficile* strain 630 comprises antibodies that bind to other variant Toxin B from other stains as described above, including 'hypervirulent' Toxin B (e.g. TcdBHV). Accordingly, in one embodiment the present invention provides a composition as described herein, wherein the antibodies that bind to a *Clostridium difficile* Toxin B further bind to a *Clostridium difficile* Toxin B of a different toxinotype to the Toxin B toxinotype of the vaccine.

In one embodiment, the antibodies that bind to a *Clostridium difficile* Toxin B are raised against a vaccine comprising a first strain Toxin B of a first strain of *Clostridium difficile*. The vaccine may comprise *Clostridium difficile* strain 630 Toxin B.

In another embodiment, the antibodies that bind to a *Clostridium difficile* Toxin B bind to a Toxin B of a second strain of *Clostridium difficile*.

In a further embodiment, the antibodies that bind to at least one *Clostridium difficile* vegetative cell antigen are raised against a vaccine comprising vegetative cells of a first strain of *Clostridium difficile*. The vaccine may comprise *Clostridium difficile* S-layer preparations. In another embodiment, the antibodies bind to SlpA.

In one embodiment, the antibodies that bind to at least one *Clostridium difficile* vegetative cell antigen bind to at least one *Clostridium difficile* vegetative cell antigen of a second strain of *Clostridium difficile*

In another embodiment, the antibodies that bind to at least one *Clostridium difficile* endospore antigen are raised against a vaccine comprising endospores of a first strain of *Clostridium difficile*. In one embodiment, the vaccine comprises *Clostridium difficile* strain KI endospores. In another embodiment, the antibodies bind to exosporium proteins.

In a further embodiment, the antibodies that bind to at least one *Clostridium difficile* endospore antigen bind to at least one endospore antigen of a second strain of *Clostridium difficile*.

As discussed above, the present invention is based in part on the demonstration that hyperimmune colostrum of the present invention that comprises antibodies that bind an antigen raised against a vaccine comprising a *Clostridium difficile* antigen is effective for the treatment and/or prophylaxis of symptoms of *C. difficile* associated disease.

The present inventors have demonstrated that hyperimmune colostrum derived from cows vaccinated with Toxin B from *C. difficile* comprises antibodies that inhibit Toxin B cytotoxicity to cells (Example 5 and FIG. 5), and that hyperimmune colostrum derived from cows vaccinated with Toxin B from *C. difficile* comprises antibodies that inhibit Toxin B cytotoxicity of Toxin B from other strains (Example 5 and FIG. 5). Importantly, hyperimmune colostrum derived from cows vaccinated with Toxin B from *C. difficile* is effective for the treatment and/or prophylaxis of *C. difficile* associated weight loss in mice and *C. difficile* associated mortality (Example 6 and FIGS. 7, 18, and 19), and the treatment of *C. difficile* associated gastrointestinal damage in mice (Example 6 and FIGS. 8, 18 and 19).

"Neutralisation" of toxin cytotoxicity means the action of a substance (e.g. an antibody) which blocks the biological action of one or more of the cytotoxins (Toxin A and/or Toxin B) of *C. difficile*. The cytotoxins biological action ("cytotoxicity") is the ability of the Toxin to kill or impair the function of mammalian cells, in particular cells of the mammalian gut epithelium. Toxin neutralising activity of a substance may be measured by its ability to prevent the death of mammalian cells grown in culture.

As discussed above, the present invention is based in part on the demonstration that antibodies that bind to at least one *Clostridium difficile* vegetative cell antigen are able to inhibit symptoms of *C. difficile* associated disease. The present inventors have also demonstrated that antibodies that bind to at least one *Clostridium difficile* vegetative cell antigen are able to inhibit *C. difficile* associated disease. In particular, hyperimmune colostrum derived from cows vaccinated with *C. difficile* endospores is effective for the treatment of *C. difficile* associated weight loss in mice, *C. difficile* associated mortality, inhibiting *C. difficile* colonisation of mice, and reducing shedding of *C. difficile* spores from infected mice (Example 10 and FIG. 11).

Accordingly, in one embodiment, the present invention provides compositions wherein the antibodies that bind to at least one *Clostridium difficile* vegetative cell antigen are raised against a vaccine comprising *Clostridium difficile* vegetative cells.

In one embodiment, the antibodies that bind to at least one *Clostridium difficile* vegetative cell antigen are raised against a vaccine comprising *Clostridium difficile* S-layer preparations. *C. difficile* expresses a crystalline or paracrystalline surface layer (S-layer) on the outer cell surface. Such S-layers comprise proteins or glycoproteins forming a regularly arranged lattice on the external surface of the bacterium, and have previously been shown to be essential for the virulence of pathogens such as *Aeromanas salmonicida* and *Campylobacter fetus*. In contrast to most bacteria which comprise one S-layer, *C. difficile* is known to comprise two superimposed paracrystalline S-layers, each composed of a glycoprotein subunit which varies slightly in apparent molecular weight among different *C. difficile* strains. Most strains of *C. difficile* express two major S-layer proteins (SLPs), one of 32-38 kDa (low-MW SLP) and a second of 42-48 kDa (high-MW SLP). The low-MW SLP appears to be immunodominant and is the antigen most commonly recognised by patients suffering from CDAD, and is the only antigen recognised in EDTA extracts of bacteria by antisera raised in rabbits against whole *C. difficile* cells (Calabi, E. et al., 2001, Mol. Microbiol., 40(5) pi 187-99, PMID: 11401722).

The S-layer of *C. difficile* consists primarily of the major S-layer protein SlpA and a family of SlpA homologues, the cell wall protein (CWP) family. In one embodiment, the antibodies bind to SlpA.

The present inventors have demonstrated that serum derived from cows vaccinated with vegetative cells of *C. difficile* comprises antibodies that bind to *C. difficile* vegetative cells (Example 11, and FIGS. 12 and 13), and that serum derived from cows vaccinated with vegetative cells of *C. difficile* comprises antibodies that bind to S-layer proteins (Example 12 and FIG. 14). FIG. 14 demonstrates the antibodies that bind to S-layer proteins of vegetative cells further bind to at least one *C. difficile* S-layer protein of a different *Clostridium difficile* strain.

Importantly, the present inventors have demonstrated hyperimmune colostrum derived from cows vaccinated with vegetative cells of *C. difficile* is effective for the treatment and/or prophylaxis of *C. difficile* associated weight loss in mice and *C. difficile* associated mortality in mice (Example 13 and FIG. 15).

As discussed above, the present inventors have demonstrated hyperimmune colostrum derived from cows vaccinated with endospores from *C. difficile* strain KI comprises antibodies that bind to endospores (Example 8 and FIG. 9), and exosporium proteins (Example 9 and FIG. 10). Importantly, hyperimmune colostrum derived from cows vaccinated with endospores from *C. difficile* is effective for the treatment and/or prophylaxis of *C. difficile* associated weight loss in mice and *C. difficile* associated mortality and inhibiting *C. difficile* colonisation of mice, and faecal shedding of *C. difficile* spores from infected animals (Example 10 and FIGS. 11 and 18).

The present inventors have also demonstrated antibodies wherein the antibodies that bind to at least one *Clostridium difficile* endospore antigen are raised against a vaccine comprising *Clostridium difficile* endospores.

In one embodiment, the endospores are *Clostridium difficile* strain KI endospores.

In one embodiment, the antibodies bind to exosporium proteins.

The present inventors have also demonstrated mice administered a composition comprising antibodies that bind to a Toxin B, antibodies that bind to at least one endospore antigen, and antibodies that bind to at least one vegetative cell antigen showed delayed weight loss and increased survival compared to mice that received non-immune colostrum.

Accordingly, in one embodiment the present invention comprises a composition comprising antibodies that bind one or more *C. difficile* antigen.

The composition may comprise antibodies that bind a Toxin B and antibodies that bind to at least one endospore antigen, antibodies that bind to a Toxin B and antibodies that bind to at least one vegetative cell antigen, antibodies that bind to at least one vegetative cell antigen and antibodies that bind to at least one endospore antigen, or antibodies that bind to a Toxin B, antibodies that bind to at least one endospore antigen, and antibodies that bind to at least one vegetative cell antigen.

The composition may comprise antibodies that bind both Toxin B and Toxin A and antibodies that bind to at least one endospore antigen, antibodies that bind to a Toxin B and Toxin A and antibodies that bind to at least one vegetative cell antigen, antibodies that bind to at least one vegetative cell antigen and antibodies that bind to at least one endospore antigen, or antibodies that bind to a Toxin B and Toxin A, antibodies that bind to at least one endospore antigen, and antibodies that bind to at least one vegetative cell antigen.

The ratio of the different antibodies in the composition may be varied according to standard methods. For example, the ratio of the first antibody to the second antibody may be about 1:1, 2:1, 3:1, 4:1 or 5:1. In embodiments wherein the composition comprises three different antibodies, the ratio of the first antibody to the second and third antibodies may be about 1:1:1 2:1:1, 3:1:1, 4:1:1, 5:1:1, 6:1:1, 7:1:1 or 8:1:1.

For example, in one embodiment, the antibodies that bind a Toxin B and antibodies that bind to at least one endospore antigen are in a 1:1 ratio.

In another embodiment, the antibodies that bind a Toxin B and antibodies that bind to at least one endospore antigen are in a 2:1 ratio.

In another embodiment, the antibodies that bind to a Toxin B, antibodies that bind to at least one endospore antigen, and antibodies that bind to at least one vegetative cell antigen are in a 1:1:1 ratio.

In another embodiment, the antibodies that bind to a Toxin B, antibodies that bind to at least one endospore antigen, and antibodies that bind to at least one vegetative cell antigen are in a 2:1:1 ratio.

In another embodiment, the antibodies that bind to a Toxin B, antibodies that bind to at least one endospore antigen, and antibodies that bind to at least one vegetative cell antigen are in a 3:1:1 ratio.

In another embodiment, the antibodies that bind to a Toxin B, antibodies that bind to at least one endospore antigen, and antibodies that bind to at least one vegetative cell antigen are in a 4:1:1 ratio.

In another embodiment, the antibodies that bind to a Toxin B, antibodies that bind to at least one endospore antigen, and antibodies that bind to at least one vegetative cell antigen are in a 5:1:1 ratio.

In another embodiment, the antibodies that bind to a Toxin B, antibodies that bind to at least one endospore antigen, and antibodies that bind to at least one vegetative cell antigen are in a 6:1:1 ratio.

In another embodiment, the antibodies that bind to a Toxin B, antibodies that bind to at least one endospore antigen, and antibodies that bind to at least one vegetative cell antigen are in a 7:1:1 ratio.

In another embodiment, the antibodies that bind to a Toxin B, antibodies that bind to at least one endospore antigen, and antibodies that bind to at least one vegetative cell antigen are in a 8:1:1 ratio. Importantly, the present inventors have demonstrated the antibodies of the present invention can be derived from hyperimmune material.

Accordingly, in one embodiment, the antibodies are derived from hyperimmune material.

According to one specific embodiment, the hyperimmune material-derived antibodies that bind to *C. difficile* antigens may comprise monomeric, dimeric or multimeric immunoglobulin selected from the group consisting of IgG, IgA and IgM and any fragments thereof. In ruminants, the principal compositional difference between colostrum and mature milk is the very high content of colostral immunoglobulin, of which IgG class makes up 80-90%.

Thus, according to a specific embodiment, the hyperimmune material-derived antibodies that bind to *C. difficile* antigens of the invention mainly comprise IgG, specifically, IgG1 and IgG2.

The term "Immunoglobulin G" (IgG) as used herein, is a multimeric immunoglobulin, built of two heavy chains and two light chains. Each complex has two antigen binding sites. This is the most abundant immunoglobulin and is approximately equally distributed in blood and in tissue liquids, constituting 75% of serum immunoglobulins in humans. In general, the number of IgG subclasses varied widely between different species, ranging from one subclass in rabbits to seven subclasses in horses, making it difficult to find orthologues. In humans, for example, IgG1 and IgG3 are the most pro-inflammatory IgG subclasses. In mice, however, IgG2a and IgG2b are the most pro-inflammatory IgG molecules showing a greater activity than mouse IgG1 and IgG3 in many in vivo model systems.

Optionally or additionally, hyperimmune material-derived antibodies that bind to *C. difficile* antigens may comprise a secretory antibody, specifically, sIgA.

Dimeric and multimeric IgA and IgM are secreted by a number of exocrine tissues. IgA is the predominant secretory immunoglobulin present in colostrum, saliva, tears, bronchial secretions, nasal mucosa, prostatic fluid, vaginal secretions, and mucous secretions from the small intestine. IgA output exceeds that of all other immunoglobulins, making it the major antibody produced by the body daily and is the major immunoglobulin found in human milk, whey and colostrum. IgM secretion is less abundant but can increase to compensate for deficiencies in IgA secretion. J chain containing IgA is produced and secreted by plasma B immunocytes located in the lamina propria just beneath the basement membrane of exocrine cells. IgA has a typical immunoglobulin four-chain structure ($M_r$ 160,000) made up of two heavy chains ($M_r$ 55,000) and two light chains ($M_r$ 23,000). In humans, there are two subclasses of IgA. These are IgA1 and IgA2 that have one and two heavy chains, respectively. IgA can occur as monomers, dimers, trimers or multimers. In plasma, 10% of the total IgA is polymeric while the remaining 90% is monomeric. The secreted IgA binds to a $M_r$ 100,000 poly-Ig receptor positioned in the basolateral surface of most mucosal cells. The receptor-IgA complex is next translocated to the apical surface where IgA is secreted. The binding of dimeric IgA to the poly-Ig receptor is completely dependent upon the presence of a J chain. Monomeric IgA will not bind to the receptor.

The difference in function of IgG and IgA, follows the position where the molecules operate. IgA is found mainly on mucosal surfaces where there is little in the way of tissue fluid to carry immune cells and chemicals. Therefore, IgA (often as a dimer) would be preferably used for physical neutralisation of pathogens, and may be too effective at other immune functions. IgGs are present in the tissue fluid and blood where there is the full collection of leukocytes, complement system, macrophages etc. may physically neutralize a pathogen effectively and are also more effective in a communication/presentation role than IgA, i.e., they tend to induce better opsonisation by phagocytes (e.g., Killer T cells and macrophages) and switch on the complement system better.

In another embodiment, the antibodies are derived from bovine hyperimmune colostrum.

More specifically, the hyperimmune material-derived antibodies that bind to *C. difficile* antigens of the invention may be obtained from any one of colostrum, colostrum serum, hyperimmunised milk or colostrum, colostrum whey (either cheese or casein), cheese or casein whey, directly from skim milk, whole milk, or a reconstituted form of such streams.

It should be appreciated that hyperimmune material-derived antibodies that bind to *C. difficile* antigens comprised within the composition of the invention may be any fraction of colostrum. Thus, the term colostrum where used herein includes colostral milk, processed colostral-milk such as colostral milk processed to partly or completely removes one or more of fat, cellular debris, lactose and casein.

The colostrum, or milk, containing the antibodies that bind to *C. difficile* antigens and optionally, the antigen-specific antibodies may be preferably collected by milking the animal colostrum or milk thus collected can either be used directly, may be further processed, for instance to purify anti-antigen antibodies and optionally, antigen-specific antibodies. Methods for the (partial) purification of antibodies from colostrum or milk are present in the art.

It should be further appreciated that any adjuvants may be added to the compositions of the invention. Appropriate adjuvants therefore may be any antigen, antibody, glycosphingolipids, proteins, cytokines, adhesion molecules, and component that can activate or alter the function of antigen presenting cell or of any other cell related to the immune system in a direct and indirect manner.

Alternatively, the hyperimmune material-derived antibodies that bind to *C. difficile* antigens may be an affinity purified antibody or any fragment thereof. The term "antibody" is meant to include both intact molecules as well as fragments thereof, such as, for example, Fab and F(ab')$_2$, which are capable of binding antigen. Fab and F(ab')$_2$ fragments lack the Fc fragment of intact antibody, clear more rapidly from the circulation, and may have less non-specific tissue binding than an intact antibody. It will be appreciated that Fab and F(ab')$_2$ and other fragments of the antibodies useful in the present invention may be used for immuno-modulation, according to the methods disclosed herein for intact antibody molecules. Such fragments are typically produced by proteolytic cleavage, using enzymes such as papain (to produce Fab fragments) or pepsin (to produce F(ab')$_2$ fragments).

According to another embodiment, the composition of the invention may optionally further comprise colostrum component/s such as for example, alarmins, defensins, colostrinin, and any other colostrum or milk derived carbohydrates, glycolipids or any other molecules or components that may further enhance or inhibit modulation of an immune response, or any preparations, mixtures or combinations thereof. Moreover, the composition of the invention may comprise any additional adjuvant. Appropriate adjuvants therefore may be any antigen, antibody, glycosphingolipids, proteins, cytokines, adhesion molecules, and component that can activate or alter the function of antigen presenting cell or of any other cell related to the immune system in a direct and indirect manner.

In some embodiments of the composition, the composition comprises a constituent of a bird's egg, wherein the bird's egg comprises IgY specific for Toxin B, a vegetative cell antigen or an endospore antigen or a fragment thereof. Crude egg yolk may be used as an antibody source. However, avian antibodies are usually purified or concentrated from the yolk prior to use. The constituent of the bird's egg may be concentrated or purified as necessary, as is understood by those skilled in the art. In some embodiments of the composition, the composition comprises the yolk of the egg, or any IgY antibody-containing fraction thereof. The yolk is preferable to the white of the egg, as the yolk typically contains much higher concentrations of IgY than does the white. However, the white may contain concentrations of IgY sufficient for some applications.

In some embodiments of the antibody composition, the IgY is concentrated, isolated, or purified from the constituent of the bird egg. This can be accomplished by a variety of methods. In some embodiments the antibodies may be purified by the water dilution method. The precipitate may then be removed by any conventional method, including centrifugation. The supernatant can then be stored frozen, for example at −20° C. IgY can then be isolated by precipitation with ammonium sulfate and subsequent dialysis. If desired, the titre of IgY antibodies can be determined by immunoassay, for example ELISA. The water dilution method is more completely described in the well-known literature, for example by Akita and Nakai (1993), which is incorporated by reference to teach this method. Other useful methods are described for example is U.S. Pat. Nos. 4,550,019, 4,748,018, and U S Patent Publication 2004/0161427 which are hereby incorporated by reference for such teachings Commercial kits are available for example from the Promega Corporation (Madison, Wis.).

Some embodiments of the antibody composition are substantially isolated. In such embodiments a significant fraction of a non-antibody yolk component has been removed. The non-antibody yolk component may be for example the lipid component of the yolk, the carbohydrate component of the yolk, the yolk granules, the hydrophobic component of the yolk, the steroid component of the yolk, and the non-immunoglobulin protein component of the yolk. The fraction of the component removed is at least 50%. In some embodiments the removed fraction is at least 60%, 75%, 80%, 90%, 95%, 99%, or 99.9%. Greater removed fractions have the advantage of producing a more pure antibody composition. Smaller removed fractions have the advantage of requiring less processing.

Some embodiments of the antibody composition are substantially concentrated. In such embodiments the concentration of IgY will be greater in the composition than in the egg yolk. Substantially concentrated antibody compositions comprise IgY that is at least twice as concentrated as in the yolk. Some embodiments of the substantially concentrated antibody composition are concentrated by at least a factor of 3, 4, 5, 6, 7, 8, 9, 10, 100, 1000, or 10,000. More concentrated antibody compositions have the advantage of providing the same mass of antibodies in lower volume. Less concentrated antibody compositions have the advantage of requiring less processing.

The antibody compositions of the present disclosure may be processed so as to largely remove all isotypes except IgG and IgY. In some embodiments the immunoglobulin may be derived from numerous donors. Any number of donors may be used. In some embodiments, the antibodies are derived from one donor. In further embodiments, the antibodies are derived from 1-10 donors. In further embodiments, the antibodies are derived from 10-100 donors. In further embodiments, the antibodies are derived from 100-1000 donors. In still further embodiments, the antibodies are derived from over 1000 donors.

In some embodiments of the antibody composition, the composition is made by the method comprising obtaining an egg laid by a fowl previously immunized with Toxin B, a vegetative cell antigen or an endospore antigen and separating the antibody fraction from a yolk of the egg. In some embodiments of the composition the fowl has been actively immunized, for example by vaccination. The fowl is preferably a domesticated fowl. The domesticated fowl may be chicken, duck, swan, goose, turkey, peacock, guinea hen, ostrich, pigeon, quail, pheasant, dove, or other domesticated fowl. The domesticated fowl is preferably a chicken. The domesticated fowl is more preferably a domesticated chicken raised primarily for egg or meat production. The fowl may be immunized against any strain of influenza, any subtype of influenza, any type of influenza, or combinations thereof.

Use of eggs from chickens raised for egg or meat production, and which are vaccinated pursuant to this purpose, has the great advantage of using as the feedstock for the process eggs that are widely available commercially in great volumes and at very low price. Previously, animals used for the production of antibodies have been raised solely or mainly for that purpose, and maintained in small numbers at very high expense.

In some embodiments of the antibody composition, the antibody composition is made by a method comprising actively immunizing a hen with antigen, collecting eggs from the hen after an immunization period, and separating the antibody fraction from a yolk of the egg. Optionally, collecting eggs from the hen can occur continuously after the immunization period. The immunization of the bird may occur by any means known in the art. For example, a vaccine may be administered to the bird that is known to effectively elicit an immune response in birds, or that is known to effectively elicit an immune response in mammals. Many such influenza vaccines are commercially available, and can be routinely developed by those of ordinary skill in the art without undue experimentation further methods of producing IgY with a specific target are known to those skilled in the art. Such methods can be found for example in U.S. Pat. Nos. 4,550,019, 4,748,018, and U.S. Patent Publication 2004/0161427, and U.S. Pat. No. 6,537,500, which are incorporated by reference.

In one embodiment, the present invention provides a composition comprising antibodies that bind Toxin B, a vegetative cell antigen and/or an endospore antigen for use in treatment and/or prophylaxis of CDAD wherein composition is derived from avian eggs and further comprising non-hyperimmune colostrum.

In one embodiment the composition is formulated for oral administration.

According to one preferred embodiment, any of the compositions of the invention may be administered orally or by inhalation as an aerosol or by intravenous, intramuscular, subcutaneous, intraperitoneal, parenteral, transdermal, intravaginal, intranasal, mucosal, sublingual, topical, rectal or subcutaneous administration, or any combination thereof.

Orally administrated antibodies would be expected to be degraded in the gastrointestinal tract, given the low gastric pH and the presence of gastric and intestinal proteases. However, bovine colostral IgG (BCIg) has been cited as particularly resistant to GI destruction, relative to other immunoglobulins. Early studies of BCIg cited remarkable "resistance to proteolytic digestion in the intestine of a heterologous host". There is also evidence that bovine IgG1 is somewhat more resistant to proteolysis by trypsin, chymotrypsin and pepsin than other Igs. These results drove much of the early development of oral antibody therapy. More specifically, the composition of the invention may be suitable for mucosal administration, for example, pulmonary, buccal, nasal, intranasal, sublingual, rectal, vaginal administration and any combination thereof.

As indicated above, although oral administration is preferred, it should be appreciated that any other route of administration may be applicable, for example, intravenous, intravenous, intramuscular, subcutaneous, intraperitoneal, parenteral, intravaginal, intranasal, mucosal, sublingual, topical, rectal or subcutaneous administration, or any combination thereof.

Moreover, the antibodies that bind a Toxin B, a vegetative cell antigen or an endospore antigen used by the compositions and combined compositions of the invention may be prepared in preparations such as food additives, aqueous solutions, oily preparations, emulsions, gels, etc., and these preparations may be administered orally, topically, rectally, nasally, buccally, or vaginally. The preparations may be administered in dosage formulations containing conventional non-toxic acceptable carriers and may also include one or more acceptable additives, including acceptable salts, polymers, solvents, buffers, excipients, bulking agents, diluents, excipients, suspending agents, lubricating agents, adjuvants, vehicles, deliver systems, emulsifiers, dis-integrants, absorbents, preservatives, surfactants, colorants, flavourants or sweeteners. An optional dosage form of the present invention may be a powder for incorporation into beverages, pills, syrup, capsules, tablets, granules, beads, chewable lozenges or food additives, using techniques known in the art. Thus, immuno-modulating composition of the invention may be administered in a form selected from the group consisting of orally-active powders, pills, capsules, teas, extracts, dried extracts, sublinguals, sprays, dispersions, solutions, suspensions, emulsions, foams, syrups, lotions, ointments, gels, pastes, dermal patches, injectables, vaginal creams and suppositories.

Therapeutic formulations may be administered in any conventional dosage formulation. Formulations typically comprise at least one active ingredient, as defined above, together with one or more acceptable carriers thereof.

Each carrier should be both pharmaceutically and physiologically acceptable in the sense of being compatible with the other ingredients and not injurious to the patient. Formulations include those suitable for oral, rectal, nasal, or parenteral (including subcutaneous, intramuscular, intravenous and intradermal or by inhalation) administration. The formulations may conveniently be presented in unit dosage form and may be prepared by any methods well known in the art of pharmacy. The nature, availability and sources, and the administration of all such compounds including the effective amounts necessary to produce desirable effects in a subject are well known in the art and need not be further described herein.

The preparation of pharmaceutical compositions is well known in the art and has been described in many articles and textbooks, see e.g., Remington's Pharmaceutical Sciences, Gennaro A. R. ed., Mack Publishing Co., Easton, Pa., 1990, and especially pp. 1521-1712 therein, fully incorporated herein by reference.

The pharmaceutical composition of the invention can be administered and dosed in accordance with good medical practice.

The composition of the invention may comprise the active substance in free form and be administered directly to the subject to be treated. Formulations typically comprise at least one active ingredient, as defined above, together with one or more acceptable carriers thereof. Each carrier should be both pharmaceutically and physiologically acceptable in the sense of being compatible with the other ingredients and not injurious to the patient.

Formulations include those suitable for oral, nasal, or parenteral (including subcutaneous (s.c.), intramuscular (i.m.), intraperitoneal (i.p.), intravenous (i.v.) and intradermal or by inhalation to the lung mucosa) administration. The formulations may conveniently be presented in unit dosage form and may be prepared by any methods well known in the art of pharmacy. The nature, availability and sources, and the administration of all such compounds including the effective amounts necessary to produce desirable effects in a subject are well known in the art and need not be further described herein.

The pharmaceutical compositions of the invention generally comprise a buffering agent, an agent that adjusts the osmolarity thereof, and optionally, one or more pharmaceutically acceptable carriers, excipients and/or additives as known in the art. Supplementary active ingredients can also be incorporated into the compositions. The carrier can be solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants.

As used herein "pharmaceutically acceptable carrier" includes any and all solvents, dispersion media, coatings, antibacterial and antifungal agents and the like. The use of such media and agents for pharmaceutical active substances is well known in the art. Except as any conventional media or agent is incompatible with the active ingredient, its use in the therapeutic composition is contemplated.

In instances in which oral administration is in the form of a tablet or capsule, the active drug components (antibodies that bind to a *Clostridium difficile* Toxin B, antibodies that bind to at least one *Clostridium difficile* vegetative cell antigen, and/or antibodies that bind to at least one *Clostridium difficile* endospore antigen) can be combined with a non-toxic pharmaceutically acceptable inert carrier such as lactose, starch, sucrose, glucose, modified sugars, modified starches, methylcellulose and its derivatives, dicalcium phosphate, calcium sulfate, mannitol, sorbitol, and other reducing and non-reducing sugars, magnesium stearate, stearic acid, sodium stearyl fumarate, glyceryl behenate, calcium stearate and the like. For oral administration in liquid form, the active drug components can be combined with non-toxic pharmaceutically acceptable inert carriers such as ethanol, glycerol, water and the like. When desired or required, suitable binders, lubricants, disintegrating agents and colouring and flavouring agents can also be incorporated into the mixture. Stabilizing agents such as antioxidants, propyl gallate, sodium ascorbate, citric acid, calcium metabisulphite, hydroquinone, and 7-hydroxycoumarin can also be added to stabilize the dosage forms. Other suitable compounds can include gelatin, sweeteners, natural and synthetic gums such as acacia, tragacanth, or alginates, carboxymethylcellulose, polyethylene, glycol, waxes and the like.

According to one embodiment, the antibodies that bind to a *Clostridium difficile* Toxin B, antibodies that bind to at least one *Clostridium difficile* vegetative cell antigen, and/or antibodies that bind to at least one *Clostridium difficile* endospore antigen used for the invention comprises monomeric, dimeric or multimeric immunoglobulin selected from the group consisting of IgG, IgA and IgM and any fragments, mixtures or combinations thereof.

In yet another embodiment, the use according to the invention of antibodies that bind to a *Clostridium difficile* Toxin B, antibodies that bind to at least one *Clostridium difficile* vegetative cell antigen, and/or antibodies that bind to at least one *Clostridium difficile* endospore antigen is for manufacturing a composition or combined composition that optionally may further comprises colostrum, milk or milk products component/s and any adjuvant/s, preferably, alarmins, defensins, colostrinin and any preparation, mixture or combination thereof. It should be further appreciated that the composition of the invention may comprise any additional adjuvant. Appropriate adjuvants therefore may be any antigen, antibody, glycosphingolipids, proteins, cytokines, adhesion molecules, and component that can activate or alter the function of antigen presenting cell or of any other cell related to the immune system in a direct and indirect manner. It should be noted that according to certain embodiments the present invention further provides the use of colostrum or any colostrum-derived preparations in the combined compositions of the invention for enhancing an immunomodulatory effect of an immunomodulatory therapeutic agent.

The term alarmin, denotes an array of structurally diverse multifunctional host proteins that are rapidly released during infection or tissue damage, and that have mobilizing and activating effects on receptor-expressing cells engaged in host defence and tissue repair. Innate-immune mediators that have alarmin function include defensins, eosinophil-derived neurotoxin, cathelicidins and HMGB1.

Defensins are small (15-20 residue) cysteine-rich cationic proteins found in both vertebrates and invertebrates. They are active against bacteria, fungi and enveloped viruses. They consist of 15-20 amino acids including six to eight conserved cysteine residues. Cells of the immune system contain these peptides to assist in killing phagocytized bacteria, for example in neutrophil granulocytes and almost all epithelial cells. Most defensins function by penetrating the microbes cell membrane by way of electrical attraction, and once embedded, forming a pore in the membrane which allows efflux.

The term "Colostrinin", as use herein refers to a polypeptide which, in its natural form, is obtained from mammalian colostrum. Colostrinin is sometimes known as "colostrinine", and has a molecular weight in the range 16,000 to 26,000 Daltons. Colostrinin may form a dimer or trimer of sub-units (each having a molecular weight in the range 5,000 to 10,000 Daltons, preferably 6,000 Daltons), and contains mostly proline (the amount of proline is greater than the amount of any other single amino acid). Colostrinin is characterized in that it stimulates the production of cytokines, especially gamma interferon (IFN-γ), tumor necrosis factor TNF-α), interleukins (e.g. IL-6 and IL-10) and various growth factors.

In one embodiment, the antibodies are derived from hyperimmune colostrum.

The present inventors have demonstrated that when a bovine mammal is co-administered with more than one vaccine, for example a vaccine comprising *Clostridium difficile* Toxin B and a vaccine comprising *Clostridium difficile* vegetative cells, or co-administered with a vaccine comprising *Clostridium difficile* Toxin B and a vaccine comprising *Clostridium difficile* endospores, the immune response may be biased towards one of the co-administered vaccines.

Accordingly, in one embodiment the hyperimmune material is prepared by vaccination of a first lot of one or more mammals with a vaccine comprising *Clostridium difficile* Toxin B, and vaccination of a second lot of one or more mammals with a vaccine comprising *Clostridium difficile* vegetative cells and/or vaccination of a third lot of one or more mammals with a vaccine comprising *Clostridium difficile* endospores, and subsequently blending the hyperimmune material from the lots.

The administration of the composition of the present invention in order to practice the present methods of therapy is carried out by administering a therapeutically effective amount/dose of the compounds in the composition to a subject in need of such treatment or prophylaxis. The need for a prophylactic administration according to the methods of the present invention is determined via the use of the well-known risk factors as described herein.

As used herein, "patient" or "subject" includes organisms which are capable of suffering from a *C. difficile* infection or CDAD, such as but not limited to human and non-human animals.

A "therapeutically effective amount" refers to the amount of the antibody, which when administered alone or in combination to a patient for treating CDAD, or at least one of the clinical symptoms of CDAD, is sufficient to affect such treatment of the disease, or symptom. The therapeutically effective amount can vary depending, for example, on the antibody, the infection, and/or symptoms of the infection, severity of the infection, and/or symptoms of the infection, the age, weight, and/or health of the patient to be treated, and the judgment of the prescribing physician. An appropriate therapeutically effective amount in any given instance may be ascertained by those skilled in the art or capable of determination by routine experimentation. A therapeutically effective amount is also one in which any toxic or detrimental effects of the antibody are outweighed by the beneficial effects.

A "prophylactically effective amount" is any amount of the antibody that, when administered alone or in combination to a patient, inhibits or delays the onset or recurrence of the CDAD, or at least one of the clinical symptoms of CDAD. In some embodiments, the prophylactically effective amount prevents the onset or recurrence of *C. difficile* infection entirely. "Inhibiting" the onset means either lessening the likelihood of the infection's onset, or preventing the onset entirely. The term includes preventing the onset of the symptoms of the disorder in a subject at risk of developing the disorder.

Each oral dose form may, for example, comprise the colostrum equivalent of up to 20 g per day but preferably less than 1200 mg (dry weight basis), preferably less than 800 mg, preferably less than 400 mg, more preferably less than 200 mg. By colostrum equivalent we mean the amount of raw colostrum, howsoever purified, which is processed to provide the contents of a dose form.

For oral administration, the oral dose form may comprise 5 mg to 800 mg bovine colostrum powder (BCP) (dry weight basis), e.g. 5, 10, 15, 20, 25, 30, 35, 40, 45, 50, 55, 60, 70, 80, 90, 100, 125, 150, 175, 200, 225, 250, 500, 550, 600, 650, 700, 750 or 800 mg.

Suitable dosage ranges are, e.g. from about 30 mg to about 20000 mg/day, preferably 50 mg to about 5000 mg/day, more preferably 500 mg to about 5000 mg/day, or most preferably 1500 mg to about 2000 mg/day BCP (dry weight basis). In one preferred embodiment, the dose is 1800 mg/day BCP (dry weight basis).

In one embodiment the composition is formulated for administration at a dose of about 30 mg to about 10000 mg per day, or formulated for administration at a dose of about 1800 mg per day.

In one embodiment the composition is administered at a dose of about 30 mg to about 10000 mg per day, or administered at a dose of about 1800 mg per day.

In one embodiment the antibodies are present in the composition for oral administration in an amount sufficient to provide at least 30% by dry weight of the composition of IgG.

Accordingly, for oral administration, the oral dose form may comprise 1.5 mg to 240 mg IgG, e.g. 1.5, 2, 4, 6, 8, 10, 12, 14, 16, 18, 20, 25, 30, 35, 40 45, 50, 55, 60, 65, 70, 75, 80, 85, 90, 95, 100, 110, 125, 150, 175, 200, 240, 400, 600, 800 or 1000 mg IgG.

In another embodiment the antibodies are present in the composition for oral administration in an amount sufficient to provide at least 36% by weight of the composition of IgG.

Suitable dosage ranges are, e.g. from about 10 to about 3333 mg/day, preferably 20 to about 4000 mg/day, more preferably 200 to about 2000 mg/day, or most preferably 600 mg to about 800 mg/day IgG. In one preferred embodiment, the dose is 600 mg/day IgG.

In one embodiment the antibodies that bind to the antigen are present in the composition for oral administration in an amount sufficient to provide at least 5% specific IgG of the weight of IgG.

Accordingly, for oral administration, the oral dose form may comprise 0.075 mg to 12 mg specific IgG, e.g. 0.075, 0.1, 0.125, 0.15, 0.175, 0.2, 0.4, 0.6, 0.8, 1, 1.2, 1.4, 1.6, 1.8, 2.0, 2.5, 3.0, 3.5, 4.0, 4.5, 5.0, 5.5, 6.0, 6.5, 7.0, 7.5, 8.0, 8.5, 9.0, 9.5, 10.0, 11.0 or 12 mg specific IgG.

In one embodiment the antibodies that bind to the antigen are present in the composition for oral administration in an amount sufficient to provide at least 10% specific IgG of the weight of IgG.

Suitable dosage ranges are, e.g. from about 0.5 to about 167 mg/day, preferably 10 to about 150 mg/day, more preferably 15 to about 100 mg/day, or most preferably 30 mg to about 100 mg/day specific IgG. In one preferred embodiment, the dose is 30 mg/day specific IgG.

The oral dose form may be administered for about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or 31 days.

In one embodiment, the composition is administered for 30 days.

The present inventors have demonstrated that administration of the compositions of the present invention prior to infection with *C. difficile* is effective for treating and preventing symptoms of *C. difficile* associated disease, including gastrointestinal damage, *C. difficile* infection, *C. difficile* shedding in faeces and *C. difficile* associated mortality.

Examples 5 and 6 and FIGS. 5, 7, 8, 17, 18 and 19 demonstrate that administration of antibodies that bind to *C. difficile* Toxin B prior to and during/following infection with *C. difficile* is effective in treating and preventing *C. difficile* associated disease in mice, including *C. difficile* associated mortality and gastrointestinal damage.

Example 10 and FIG. 11 demonstrate that administration of antibodies that bind to *C. difficile* endospores prior to and during/following infection with *C. difficile* is effective in treating and preventing *C. difficile* associated disease, *C. difficile* associated mortality, and reducing shedding of *C. difficile* and transmission of *C. difficile* following infection.

Example 13 and FIG. 15 demonstrate that administration of antibodies that bind to *C. difficile* vegetative cells prior to and during infection with *C. difficile* is effective in treating and preventing *C. difficile* associated disease and *C. difficile* associated mortality Example 16 and FIG. 17 demonstrate that administration of combination of antibodies that bind to *C. difficile* antigens prior to and during infection with *C. difficile* are effective in treating and preventing *C. difficile* associated disease and *C. difficile* associated mortality.

Accordingly, in one embodiment the composition is administered prior to an increased risk of acquiring *C. difficile* infection.

In one embodiment the composition is administered for at least 3 days prior to an increased risk of acquiring *C. difficile* infection.

In another embodiment, the composition is administered for at least 3, 4, 5, 6, or 7 days prior to an increased risk of acquiring *C. difficile* infection.

In one embodiment the composition is administered prior to admission to a hospital or a nursing home, or at admission to a hospital or a nursing home.

In one embodiment the composition is administered during admission to a hospital or a nursing home.

In one embodiment the composition is administered to prevent re-lapse of a previous infection.

In another embodiment, a composition of the present invention is administered following infection with *C. difficile*. For example, a composition of the present invention can be administered at least 2 hours following infection, at least 4 hours following infection, at least 12 hours following infection or at least 24 hours following infection with *C. difficile*.

The oral dose form preferably comprises colostrum derived from the hyperimmune colostrum and/or colostrum which has been added to the polyclonal antibodies in accordance with the teaching of PCT/AU03/00348 (Pub. No.: WO/2003/080082). The oral dosage form may also comprise a buffer system such as that disclosed in PCT/AU2005/001746 (Pub. No.: WO/2006/053383). The contents of these applications are incorporated herein by reference.

The magnitude of prophylactic or therapeutic dose of the active ingredients can, of course, vary with the nature of the severity of the condition to be treated. It can also vary according to the age, weight and response of the individual patient, and may be administered in subject in single or divided doses. On the other hand, it may be necessary to use dosages outside the ranges provided herein in some cases.

In one aspect, the present invention provides a method for the treatment and/or prophylaxis of at least one symptom of *Clostridium difficile* associated disease in a subject, said method comprising administering to the subject a composition comprising mammalian or avian antibodies, wherein the antibodies comprise: a) antibodies that bind to a *Clostridium difficile* Toxin B; and b) antibodies that bind to at least one *Clostridium difficile* vegetative cell antigen, and/or antibodies that bind to at least one *Clostridium difficile* endospore antigen.

The present invention will now be more fully described by reference to the following non-limiting Examples.

EXAMPLE 1

Determination of Infectious Dose of *C. difficile* Endospores for In Vivo Experiments Two independent mouse trials were performed in order to determine the minimum infectious dose of KI endospores that can be administered to mice that results in measurable *C. difficile* associated disease.

For these studies, groups of 3 mice were infected by oral gavage with $10^1$, $10^2$, $10^3$, $10^4$, $10^5$ or $10^6$ endospores generated from the *C. difficile* KI strain. Mice were monitored for morbidity (as measured by weight loss) and colonisation (as measured by spore shedding), and were humanely sacrificed at different time points (ranging between 12 and 96 hours). *C. difficile* associated disease in mice was also examined using histopathology.

FIG. 1 shows infection of C57/BL6 mice with $10^3$ KI endospores resulted in measurable *C. difficile* associated disease (weight loss)

FIG. 2 shows infection of C57/BL6 mice with $10^3$ KI endospores resulted in measurable colonisation with *C. difficile* (as determined by spore shedding in the faeces).

FIG. 3 shows histopathologic change in the caecum and colon of infected mice, indicating that a dose of $10^3$ endospores is sufficient for causing severe *C. difficile* associated gastrointestinal damage after 48 hrs of infection.

These results indicate that the infectious dose of endospores can be reduced to $10^3$ endospores per mouse.

EXAMPLE 2

Production of Antibodies that Bind to a *C. difficile* Antigen

Preparation of Antigen

The procedures for preparing microbe or microbial product-containing antigen reported in Pub. No. WO/2004/078209 International Application No. PCT/AU2004/000277 (the contents of which are herein incorporated by reference), were used with modification.

In brief, bacterial antigens for the production of the vaccines were prepared from *C. difficile*. The following antigens were produced:
1. *C. difficile* Toxin B
2. *C. difficile* vegetative cells
3. *C. difficile* endospores
4. *C. difficile* S-layer preparations Vaccines were made by emulsifying an equal volume of each antigen with the same volume of Montanide™ ISA206VG adjuvant ( an NRA-approved veterinary immunostimulant composition containing esters of octadecenoic acid and anhydromannitol in an oily solution, manufactured by Seppic and supplied by Tall Bennett of Australia).

1. Toxin B

Recombinant *C. difficile* Toxin B from strain 630 was used as an antigen. In brief, 2×500 ml volumes of Terrific broth K⁺ phosphate+50 mg/ml kanamycin in 2 L flask inoculated with 5 ml each of *E. coli* BL21 cells expressing toxB (clone CSB1 (CSB4P×2B1) (toxB(NIX):PET30R: BL21(DE3)) overnight culture (1:100 dilution), incubated 37° C., 225 rpm. Toxin B expression was induced at 3½ hours with 0.1 mm IPTG final concentration (40 ul or 0.5M IPTG/flask), incubated at 250 rpm, 37° C. for 4.5 hours. Cultures were centrifuged to pellet culture in 250 ml buckets in GSA rotor and Sorvall centrifuge at 16,000×g for 15 minutes 4° C. Supernatant was discarded and pellets stored at −20° C. Pellets were resuspended in Solution I (3×40 ml volumes), incubated on a rotating wheel at 4° C. overnight at slow speed, sonicated using a large probe at low setting (approximately 50) for 20 second bursts with 40 second rests on ice), centrifuged in SS34 rotor in 50 ml buckets at 11,000 for 15 minutes at 4° C. Supernatants were pooled and proffinity nickel resin added, and stirred slowly overnight at 4° C., centrifuged in 50 ml volumes to collect resin at 100×g, 5 minutes at room temperature, no brake, and flowthrough retained, washed with 2×50 ml volumes of Solution II, centrifuged as before, eluted in, 4.5 ml of Solution III, collected in 4 fractions (fraction 1=05 ml; 2=2 ml, 3=1 ml each), neutralised with a few drops of 0.1 N NaOH, and stored at 4° C.

Toxin B purified from the culture supernatant of a hypervirulent Australian isolate of *C. difficile*, strain KI, was also used. Toxin B isolated from the culture supernatant of a naturally occurring Toxin A negative and Toxin B positive Australian animal isolate of *C. difficile*, strain AI35, was also used. Toxins were partially purified as follows: Briefly, *C. difficile* was grown overnight on Heart Infusion agar supplemented with 1% (w/v) sodium taurocholate, 1.5% (w/v) glucose and 1% (w/v) L-cysteine. Colonies were used to inoculate 500 mL volumes of Tryptone Yeast broth (3.0% tryptone, 2.0% yeast extract and 0.1% sodium thioglycolate) and the cultures were grown for 3 days, after which time the cells were pelleted by centrifugation (10,000 g, 15 min, 4° C.). For strain KI Toxin B, 1 L of supernatant was concentrated down to a final volume of 20 ml (X50). For strain AI35 Toxin B, 3 L of supernatant was concentrated down to a final volume of 20 ml (X150). The culture supernatants were then filter sterilized (0.45-µm filters, followed by 0.2-µm filters) and concentrated using a 100,000 MWCO concentrating cassette (Sartorius). The supernatants were dialysed using PBS during concentration. The supernatants were treated with formaldehyde (1% final volume) overnight at 4° C., followed by further dialysis and concentration to remove excess formaldehyde prior to cow vaccination. Toxin supernatant was adjusted to 1 mg/ml (as determined by BCA assay) and mixed with adjuvant for cow vaccination.

2. *C. difficile* Vegetative Cells

KI endospores were germinated on HIS agar containing 10% w/v sodium taurocholate (24-48 hours incubation anaerobically at 37° C.). KI was passaged twice on HIS agar supplemented with 10% w/v sodium taurocholate (24 hours incubation anaerobically at 37° C.). A colony was selected from the final plate and used to inoculate HIS broth (5 ml) containing 10% w/v sodium taurocholate. This broth was then serially diluted to $10^{-7}$ and all 8 cultures were incubated overnight (approximately 10 hours) anaerobically at 37° C. After incubation, the optical density (OD) of all cultures was measured at 600 nm. A 1:100 dilution of the culture in its mid-exponential phase of growth ($OD_{600nm}$ 0.40-0.70) was used to inoculate HIS broth (20 ml) containing 10% w/v of sodium taurocholate and grown to $OD_{600nm}$ 0.50. A 1:100 dilution of this culture was used to inoculate HIS broth (500 ml) containing 10% w/v sodium taurocholate and grown to $OD_{600nm}$ 0.50-0.70. To harvest cells, cultures were centrifuged at 3200×g for 20 minutes at 4° C. The cells were washed 3 times using PBS (centrifuging at 3200×g for 20 minutes at 4° C. in between washes). The cells were fixed using 1% formaldehyde in PBS overnight at 4° C. After fixation, the cells were washed 3 times using PBS to remove the formaldehyde. They were resuspended in a final volume of 20 ml then adjusted to approximately $2.25 \times 10^{10}$ cells/ml. 1 mL of cells were used for vaccinations.

3. *C. difficile* Endospores

*C. difficile* endospores were prepared by routine methods. In brief, *C. difficile* strains were grown in 500 mL volumes of Tryptone Yeast broth (3.0% tryptone, 2.0% yeast extract and 0.1% sodium thioglycolate) anaerobically at 37° C. for 7-10 days to induce sporulation. The endospores were then harvested by centrifugation at 7000 rpm for 20 minutes at 4° C. and washed 4 to 6 times with sterile $dH_2O$ PBS prior to heat-shocking at 60° C. for 20 min to kill surviving vegetative cells and stored in sterile $dH_2O$ at 4° C. until required. The endospores were then quantified before use by plating tenfold serial dilutions of the endospores onto taurocholate-cefoxitin-D-cycloserine-fructose-agar (TCCFA). Each cow received $2.8 \times 10^9$ endospores at vaccination.

4. *C. difficile* S-Layer Preparations

To prepare S-layer preparations, overnight cultures of KI are grown using HIS broth. Cells are harvested by centrifugation at 3200×g for 20 minutes at 4° C. Cells were washed once with PBS, then resuspended in 0.04 volumes of 0.2M glycine pH 2.2 and incubated, mixing end over end, for 30 minutes at room temperature. After incubation, the sample was centrifuged at 13,000 rpm for 10 minutes and the supernatant containing S-layer proteins was collected. The supernatant was neutralised using 2M Tris pH 9.0. The SLP was dialysed overnight in PBS with multiple changes of buffer. Total protein was quantified using a BCA assay and adjusted to 1.0 mg/ml. 0.3% formalin was used for fixation and left for 3 days.

Preparation of Hyperimmune Colostrum Comprising Antibodies

The procedures for preparing anti-microbe or microbial product antibodies from vaccinated cattle reported in Pub. No. WO/2004/078209 International Application No. PCT/AU2004/000277 (the contents of which are herein incorporated by reference) were used.

In brief, the antigen vaccine was administered to dairy cows during the last eight weeks of gestation. Colostrum was collected from immunised cows up to 48 hours post calving. The colostrum was collected into individual containers and kept frozen until processing. Briefly, the milk fat was removed by centrifugation and skim milk was pasteurized at 63.5° C. for 30 minutes. Colostrum is chilled rapidly to 4° C. (on ice) then left overnight at 4° C., centrifuged, filtered through Kimwipes and concentrated until 30-35% of the original volume is removed using a 30,000 MWCO cassette. Following concentration (removal of lactose and salts), diafiltration is performed by adding MilliQ water, the MilliQ water is added to the concentrated colostrum to return the volume to the original amount. The colostrum is concentrated again to approximately 60% of the original volume. The colostrum is either aliquoted and stored at -20° C. or freeze dried and stored at room temperature until required.

EXAMPLE 3

Detection of Antibodies that Bind to *C. difficile* Toxin B by ELISA

Recombinant *C. difficile* Toxin B from strain 630 was used in an antigen vaccine, cows immunised and hyperimmune colostrum purified as described in Example 2.

Plates were coated with purified recombinant Toxin B from strain 630 [1 ug/ml] in carbonate buffer [pH 9.6], 100 µl/well, overnight, 4° C. Toxin B was prepared in 10% glycerol, at 1.94 mg/ml. Plates were washed 6 times in PBS-0.05% Tween® (polyoxyethylene (20) sorbitan monolaurate $C_{58}H_{114}O_{26}$)) buffer, comprising 137 mM NaCl, 1.5 mM KH2PO, 8 mM Na2HPO4, pH 7.4. 100 µl of each test colostrum prepared from cows as described in Example 2 were diluted in PBS-Tween® containing 12 mg/ml casein, were added to each well and incubated at 37° C. for 1 h. Plates were washed 6 times in PBS-Tween® buffer, after which 100 µl goat anti-bovine IgG-peroxidase conjugate (Southern Biotechnology Associates, Inc., Birmingham, Ala., USA), diluted 1:10000 in PBS-Tween®-casein,were added to each well. Plates were incubated for 1 h at 37° C. and washed 6 times. 100 µl peroxidase substrate (Kirkegaard and Perry Lab. Inc., Gaithersburg, Md., USA) were added to each well and left at room temperature until colour developed (7 minutes). The reaction was stopped by the addition of 2 M sulphuric acid and the plates were read in a Diagnostics Pasteur LP400 plate reader (Sanofi, Mames-la-Coquette, France) at 450 nm-630 nm. Results were expressed as the mean net O.D. (after subtraction of the blank reaction) of duplicate wells assayed on at least two separate occasions.

Endpoint titres of antibodies that bind to *C. difficile* Toxin B from three cows were taken respectively. This data indicates that bovine hyperimmune colostrum raised against a vaccine comprising *C. difficile* Toxin B comprises antibodies that bind to *C. difficile* Toxin B.

Furthermore, the total IgG antibody concentration of a bovine hyperimmune colostrum composition comprising antibodies that bind to *C. difficile* Toxin B was found to be between 199 to 415 mg of IgG per gram of bovine colostrum powder (BCP) as determined by IgG ELISA.

FIG. 6 demonstrates bovine hyperimmune colostrum raised against a vaccine comprising recombinant *C. difficile* Toxin B comprises antibodies that bind to *C. difficile* Toxin B.

FIG. 6 also shows hyperimmune colostrum derived from cows vaccinated with recombinant Toxin B from *C. difficile* strain 630 comprises IgG antibodies.

EXAMPLE 4

Detection of Antibodies that Bind to *C. difficile* Toxin B by Immunoblot

Colostrum derived from cows vaccinated with recombinant Toxin B (strain 630 Toxin B) as described above at Example 2 was examined for its ability to bind to commercial purified historical Toxin A (Toxin A-Hist), purified historical Toxin B (Toxin B-Hist) or hypervirulent strain 027 Toxin B (Toxin B-HV).

FIG. 4 demonstrates bovine hyperimmune colostrum raised against a vaccine comprising C. difficile Toxin B comprises antibodies that bind to C. difficile Toxin B.

Lanes were loaded with 50 µg of purified protein, fractionated by SDS-PAGE, transferred onto nitrocellulose membranes and subsequently probed with antibodies that were isolated from colostrum from an unimmunised cow or a cow vaccinated with recombinant Toxin B.

The colostrum from the cow vaccinated with Toxin B of a first strain (strain 630) contained antibodies that bind to Toxin B of other strains; Toxin B that was purified from a historical strain of C. difficile and Toxin B purified from a hypervirulent strain of C. difficile (FIG. 4B). The antibodies did not bind Toxin A (FIG. 4B).

Furthermore, when tested against a panel of toxins isolated from the culture supernatants of various other C. difficile strains, antibodies that bind to C. difficile Toxin B of a first strain were shown to bind C. difficile Toxin B of further (different) C. difficile strains (FIGS. 4D and E).

This demonstrates that the antibodies derived from cows that were vaccinated with recombinant 630 Toxin B are able to bind to Toxin B of other C. difficile strains.

EXAMPLE 5

Demonstration that Antibodies that Bind to C. difficile Toxin B Neutralise Toxin B Cytotoxicity Antibodies that bind to C. difficile Toxin B as described above were examined for their ability to neutralise Toxin B cytotoxicity in vitro.

Cytotoxicity assays were performed using Vero cells ($1 \times 10^4$ cells/well) in a 96 well plate. Different amounts of commercial purified Toxin B (200 pg, 100 pg, 50 pg or 10 pg/well) were incubated for 90 minutes with IgG purified from colostrum from an unvaccinated cow as well as a cow vaccinated with recombinant Toxin B. Commercial anti-Toxin B antibody was used as a positive control. 200 pg, 100 pg, 50 pg or 10 pg/well of commercial toxin alone were also included as controls. Following incubation of the toxin with the colostrum IgG, the different mixtures were added to the Vero cells (100 µl/well). The cells were then incubated overnight before being scored for cytopathic effect (CPE).

FIG. 5 demonstrates that antibodies that bind to Toxin B of strain 630 neutralise the cytotoxicity of C. difficile Toxin B purified from a second, hypervirulent 027 strain (TcdB-HV), of C. difficile.

FIG. 5 shows photomicrographs taken of Vero cells after exposure to toxin with or without prior incubation with colostrum IgG antibodies. Panel 5A shows Vero cells not exposed to TcdB-HV; B, Vero cells exposed to TcdB-HV; C, Vero cells that were exposed to toxin that had been pre-incubated with purified IgG from non-immune colostrum; D, Vero cells that were exposed to toxin that had been pre-incubated with 630 Toxin B colostrum antibodies and E, Vero cells that were exposed to toxin that had been pre-incubated with commercial anti-Toxin B antibody; Cell death is seen by cell rounding.

This demonstrates the antibodies that bind to a C. difficile Toxin B are able to neutralise the cytopathic effect of C. difficile Toxin B as well as neutralise the cytopathic effect of Toxin B from a different C. difficile strain.

EXAMPLE 6

Administration of Antibodies that Bind to C. difficile Toxin B is Effective in Preventing C. difficile Associated Disease, Including Gastrointestinal Damage and C. difficile Associated Mortality in Mice Antibodies that bind to C. difficile Toxin B were examined for their ability to prevent C. difficile associated disease in mice.

Groups of male, 6-7 week old, C57/BL6 mice were pre-treated with an antibiotic cocktail for 7 days. Mice were administered either non-immune or Toxin B colostrum (in the drinking water) for 2 days prior to infection with C. difficile KI endospores ($10^3$ endospores/mouse) as described in Example 1. Mice were kept on colostrum during the course of the trial and monitored for weight loss and survival. FIG. 5 shows data pooled from three independent mouse trials. N≥14 mice/group.

To examine C. difficile associated disease, weight loss was examined in mice administered either non-immune colostrum or bovine hyperimmune colostrum comprising antibodies that bind to C. difficile Toxin B. FIG. 7 shows antibodies that bind to a C. difficile Toxin B prevent C. difficile associated disease as measured by weight loss.

To examine C. difficile associated mortality, survival of mice was examined in mice administered either non-immune colostrum or bovine hyperimmune colostrum comprising antibodies that bind to a C. difficile Toxin B. FIG. 7 shows antibodies that bind to a C. difficile Toxin B prevent C. difficile associated mortality.

To further examine the gastrointestinal damage during C. difficile infection, the colon and caecum of mice were collected and analysed for gastrointestinal damage using histopathology. Representative images of sections of tissue are shown in FIG. 8, stained with PAS/alcian blue.

As can be seen in FIG. 8, mice administered non-immune colostrum displayed severely damaged colonic tissue compared to mice administered bovine hyperimmune colostrum comprising antibodies that bind to C. difficile Toxin B prior to and during infection, or compared to the uninfected (PBS) control mice.

These results demonstrate that bovine hyperimmune colostrum comprising antibodies that bind to C. difficile Toxin B prevents damage to the gastrointestinal tract of infected animals, as measured by histopathologic change.

EXAMPLE 7

Production of Hyperimmune Colostrum Comprising Antibodies that Bind to C. difficile Toxin B Two cows have been vaccinated with Toxin B concentrated from C. difficile culture supernatants from the hypervirulent Australian strain KI. Furthermore, two cows have been vaccinated with supernatant toxin isolated from a naturally occurring Toxin A negative and Toxin B positive Australian animal isolate of C. difficile, strain AI35 as described in Example 2.

Antibodies that bind to Toxin B are detected using ELISA and Immunoblot, as described above in Examples 3 and 4, respectively.

Antibodies that bind to C. difficile Toxin B are examined for their ability to bind Toxin B by Western blot and their ability to neutralise Toxin B cytotoxicity as described in Example 5, above.

Antibodies that bind to *C. difficile* Toxin B are examined for their ability to prevent measures of *C. difficile* associated disease and *C. difficile* associated mortality in mice as described in Example 6, above.

EXAMPLE 8

Detection of Antibodies in Hyperimmune Colostrum that Bind to *C. difficile* Endospores by ELISA Colostrum from cow #7003 (vaccinated with *C. difficile* strain KI endospores, as describe in Example 2, above) was prepared and the presence of antibodies that bind to *C. difficile* endospores was confirmed by ELISA.

For ELISA, wells were coated with $10^4$ K1 strain endospores/well and incubated with 4-fold serial dilutions (starting from 1:250 dilution) of either non-immune or KI spore colostrum.

The antibody titre for the KI spore colostrum was determined to be greater than 256,000, as shown in FIG. 9. This was considered a strong antibody response.

Furthermore, the total IgG antibody concentration for this colostrum was found to be 65.57 mg/mL as determined using a protein G binding column.

FIG. 9 demonstrates the production of antibodies that bind to *C. difficile* endospores by ELISA, demonstrating that antibodies that bind to *C. difficile* endospores were produced in bovine hyperimmune colostrum.

EXAMPLE 9

Detection of Antibodies that Bind to *C. difficile* Endospore Antigens in Hyperimmune Colostrum by Immunoblot Hyperimmune colostrum derived from cows vaccinated with *C. difficile* strain KI endospores was examined for its ability to bind to exosporium proteins.

Exosporium from the surface of KI endospores was extracted, fractioned using SDS-PAGE, transferred onto nitrocellulose membranes and subsequently probed with hyperimmune colostrum from an unimmunised cow or a cow vaccinated with *C. difficile* strain KI endospores.

As shown in FIG. 9, hyperimmune colostrum raised against a vaccine comprising *C. difficile* strain KI endospores antigen contained antibodies that bind to exosporium proteins of *C. difficile* endospores (FIG. 9B). In contrast, there were no antibodies in the non-immune colostrum capable of binding exosporium proteins.

This data indicates that bovine hyperimmune colostrum raised against a vaccine comprising *C. difficile* endospores comprises antibodies that bind to *C. difficile* exosporium proteins, and the colostrum comprises antibodies specific to the KI spore surface.

EXAMPLE 10

Administration of Antibodies that Bind to *C. difficile* Endospores is Effective in Treating and Preventing *C. difficile* Associated Disease, Decreasing *C. difficile* Associated Mortality, and Reducing *C. difficile* Shedding in Faeces and Transmission of *C. difficile* Following Infection in Mice Antibodies that bind to *C. difficile* endospores were examined for their ability to prevent measures of *C. difficile* associated disease such as *C. difficile* associated weight loss, mortality, and shedding of *C. difficile* spores.

Groups of male, 6-7 week old, C57/BL6 mice were pre-treated with an antibiotic cocktail for 7 days. Mice were administered either non-immune colostrum or antibodies that bind to *C. difficile* endospores ("KI spore colostrum") (in the drinking water) for 2 days prior to infection with *C. difficile* KI endospores ($10^3$ endospores/mouse). Mice were kept on colostrum during the course of the trial and monitored for weight loss, survival and endospore shedding in faeces. FIG. 10 shows data from a single mouse trial. N=5 mice/group.

To examine *C. difficile* associated morbidity, weight loss was examined in mice administered either non-immune colostrum or bovine hyperimmune colostrum comprising antibodies that bind to *C. difficile* endospores. FIG. 11 shows antibodies that bind to *C. difficile* endospores delay *C. difficile* associated morbidity as measured by weight loss. The mice that received non-immune colostrum rapidly lost weight and succumbed to infection by 48 hrs.

To examine *C. difficile* associated mortality, survival was examined in mice administered either non-immune colostrum or bovine hyperimmune colostrum comprising antibodies that bind to *C. difficile* endospores. FIG. 11 shows antibodies that bind to *C. difficile* endospores decrease *C. difficile* associated mortality.

To examine *C. difficile* associated disease, bacterial colonisation was examined in mice administered either non-immune colostrum or bovine hyperimmune colostrum comprising antibodies that bind to *C. difficile* endospores. FIG. 11 shows antibodies that bind to *C. difficile* endospores reduce bacterial colonisation as measured by a decrease in endospore numbers in the faeces of mice at 24 hours. Furthermore, FIG. 11 shows antibodies that bind to *C. difficile* endospores to reduce the numbers of *C. difficile* endospores in the faeces of mice up until the time of sacrifice. The reduced shedding of infective *C. difficile* spores is expected to diminish transmission of *C. difficile* to a subsequent naïve animal.

This data indicates that mice administered bovine hyperimmune colostrum raised against a vaccine comprising *C. difficile* endospores comprising antibodies that bind to *C. difficile* exosporium proteins delayed weight loss, reduced bacterial colonisation at 24 hrs post-infection and increased survival compared to mice that received non-immune colostrum.

EXAMPLE 11

Detection of Antibodies that Bind to *C. difficile* Vegetative Cells by ELISA

*C. difficile* strain KI vegetative cells were used in an antigen vaccine, cows immunised, and serum taken and hyperimmune colostrum purified as described in Example 2.

Each well was coated with $1\times10^6$ KI vegetative cells and incubated with 4-fold serial dilutions (starting from a 1:50 dilution of serum) of #7006 third bleed serum.

FIG. 12 demonstrates the antibody titre for this serum was determined to be 64,000.

This data demonstrates bovine serum raised against a vaccine comprising *C. difficile* vegetative cells comprises antibodies that bind to *C. difficile* vegetative cells.

EXAMPLE 12

Detection of Antibodies that Bind to *C. difficile* Vegetative Cells by Immunoblot, and Identification of Immunodominant Antigens FIG. 13 demonstrates bovine serum raised against a vaccine comprising *C. difficile* vegetative cells comprises antibodies that bind to *C. difficile* vegetative cell antigens.

Immunoblotting was performed in order to detect antibodies directed against *C. difficile* vegetative cells. Whole cell lysates from *C. difficile* strain KI (the strain the antibodies were generated against) as well as other clinically relevant human and animal *C. difficile* isolates were loaded on a 12% SDS-PAGE gel. After transfer to nitrocellulose, the membranes were probed with either the pre-bleed or $3^{rd}$ bleed (1:10,000) from cow #7006.

As shown in FIG. 13, antibodies that bind to *C. difficile* vegetative cell antigens were detected. Importantly, the antibodies generated against this hypervirulent strain appeared cross-reactive to vegetative cells of different isolates of *C. difficile*.

In particular, dominant protein bands are visible in the membrane probed with serum from the $3^{rd}$ bleed (FIG. 13B) that are absent from the membrane probed with pre-bleed serum (FIG. 13A).

To identify the dominant protein bands to determine whether these proteins could be used as immunodominant antigens for further vaccine development, two bands of approximately 49 kDa and 35 kDa from KI vegetative cell material were excised from a SDS-PAGE gel and sent to APAF for 1D nanoLC ESI MS/MS analysis. They were identified as the high molecular weight and low molecular weight components of SlpA, the major protein located on the *C. difficile* S-layer.

Immunoblots using extracted SlpA from KI vegetative cells (FIG. 14) were performed to confirm that the antibodies are against S-layer proteins. The identification of these proteins has been confirmed by mass spectrometry of excised bands from an SDS-PAGE gel loaded with S-layer preparations (SLP).

This data indicates that bovine serum raised against a vaccine comprising *C. difficile* vegetative cells comprises antibodies that bind to *C. difficile* S-layer proteins, and the serum includes antibodies that bind to SlpA.

EXAMPLE 13

Administration of Antibodies that Bind to *C. difficile* Vegetative Cells is Effective in Treating and Preventing *C. difficile* Associated Disease and *C. difficile* Associated Mortality in Mice

*C. difficile* strain KI vegetative cells were used in an antigen vaccine, cows immunised, and hyperimmune colostrum purified as described in Example 2.

Antibodies that bind to *C. difficile* vegetative cells were examined for their ability to prevent measures of *C. difficile* associated disease such as morbidity and mortality in mice.

Groups of male, 6-7 week old, C57/BL6 mice were pre-treated with an antibiotic cocktail for 7 days. Mice were administered either non-immune colostrum or antibodies that bind to *C. difficile* vegetative cells ("Vegetative cell colostrum") for 2 days prior to infection with *C. difficile* KI endospores ($10^3$ endospores/mouse). Mice were kept on colostrum during the course of the trial and monitored for weight loss, survival and vegetative cell/endospore shedding. Data below is pooled from two independent mouse trials (N=10 mice/group).

To examine *C. difficile* associated morbidity, weight loss was examined in mice administered either non-immune colostrum or bovine hyperimmune colostrum comprising antibodies that bind to *C. difficile* vegetative cells.

FIG. 15 shows that mice that were administered bovine hyperimmune colostrum comprising antibodies that bind to *C. difficile* vegetative cells showed delayed weight loss compared to mice that received non-immune colostrum. The mice that received non-immune colostrum rapidly lost weight and succumbed to infection by 36 hrs.

To examine *C. difficile* associated mortality, survival was examined in mice administered either non-immune colostrum or bovine hyperimmune colostrum comprising antibodies that bind to *C. difficile* vegetative cells. FIG. 15 shows antibodies that bind to *C. difficile* vegetative cells decrease *C. difficile* associated mortality.

This data indicates that mice administered antibodies that bind to *C. difficile* vegetative cells prepared in bovine hyperimmune colostrum showed delayed weight loss and increased survival compared to mice that received non-immune colostrum.

EXAMPLE 14

Optimisation of Vegetative Cell Antigen Preparation for Bovine Vaccines

In order to minimise the possible number of endospores present in the vegetative cell preparations and thereby maximise the amount of antibodies against vegetative cells (rather than endospores) present in the colostrum, the vegetative cell preparation protocol for the preparation of the cow vaccines is as follows:

KI endospores were germinated on HIS agar containing 10% w/v sodium taurocholate (24-48 hours incubation anaerobically at 37° C.). KI was passaged twice on HIS agar supplemented with 10% w/v sodium taurocholate (24 hours incubation anaerobically at 37° C.). A colony was selected from the final plate and used to inoculate HIS broth (5 ml) containing 10% w/v sodium taurocholate. This broth was then serially diluted tenfold to $10^{-7}$ and all 8 cultures were incubated overnight (approximately 10 hours) anaerobically at 37° C. After incubation, the optical density (OD) of all cultures was measured at 600 nm. A 1:100 dilution of the culture in its mid-exponential phase of growth ($OD_{600nm}$ 0.40-0.70) was used to inoculate HIS broth (20 ml) containing 10% w/v of sodium taurocholate and grown to $OD_{600nm}$ 0.50. A 1:100 dilution of this culture was used to inoculate HIS broth (500 ml) containing 10% w/v sodium taurocholate and grown to $OD_{600nm}$ 0.50-0.70. To harvest cells, cultures were centrifuged at 3200×g for 20 minutes at 4° C. The cells were washed 3 times using PBS (centrifuging at 3200×g for 20 minutes at 4° C. in between washes). The cells were fixed using 1% formaldehyde in PBS overnight at 4° C. After fixation, the cells were washed 3 times using PBS to remove the formaldehyde. They were resuspended in a final volume of 20 ml then adjusted to approximately $2.25 \times 10^{10}$ cells/ml. The cells were enumerated using a haemocytometer. Cows #7028 and #7029 were immunised with 1 ml of this vaccine, and hyperimmune colostrum purified as described in Example 2.

ELISAs have been performed on the processed colostrum to determine antibody titre of antibodies that bind to vegetative cells. Each well was coated with $1 \times 10^6$ KI vegetative cells and incubated with 4-fold serial dilutions.

FIG. 16 demonstrates the antibody titre for cows #7028 and #7029 are 16,000-64,000 and 256,000 respectively.

This data demonstrates the production of antibodies that bind to *C. difficile* vegetative cells by ELISA, demonstrating that antibodies that bind to *C. difficile* vegetative cells were produced in bovine hyperimmune colostrum.

EXAMPLE 15

Identification of Novel Vaccine Antigens Using Bovine Serum Comprising Antibodies that Bind to Vegetative Cell Antigens As demonstrated in Example 12, the S-layer, specifically SlpA, was identified as the immunodominant antigen in the vegetative cell antigen vaccines. To maximise the amount of specific antibody in the colostrum, a cow (#7020) was immunised with S-layer preparation (SLP).

The protocol for this vaccine is described at Example 2, above. In brief, overnight cultures of KI are grown using HIS broth. Cells are harvested by centrifugation at 3200×g for 20 minutes at 4° C. Cells were washed once with PBS, then resuspended in 0.04 volumes of 0.2M glycine pH 2.2 and incubated, mixing end over end, for 30 minutes at room temperature. After incubation, the sample was centrifuged at 13,000 rpm for 10 minutes and the supernatant containing S-layer proteins was collected. The supernatant was neutralised using 2M Tris pH 9.0. The SLP was dialysed overnight in PBS with multiple changes of buffer. Total protein was quantified using a BCA assay and adjusted to 1.0 mg/ml. 0.3% formalin was used for fixation and left for 3 days.

Cow #7020 was given 1 mg SLP per vaccination dose.

Antibodies that bind SLP are detected using ELISA and Immunoblot, as described above in Examples 3 and 4, respectively.

Antibodies that bind to *C. difficile* SLP are examined for their ability to prevent measures of *C. difficile* associated disease such as morbidity and mortality in mice as described in Example 6, above.

EXAMPLE 16

Administration of Combinations of Antibodies that Bind to *C. difficile* Antigens are Effective in Treating and Preventing *C. difficile* Associated Disease in Mice Combinations of antibodies that bind to *C. difficile* were examined for their ability to prevent measures of *C. difficile* associated disease such as morbidity and mortality in mice. Different combinations and ratios of hyperimmune colostrum comprising antibodies that bind Toxin B (#7010), endospore (#7003) or vegetative cell (#7006) colostrum were mixed together before administering to mice.

The different combinations of bovine colostrum were as follows:

1. Antibodies that bind a Toxin B and antibodies that bind to at least one endospore antigen (1:1 ratio)
2. Antibodies that bind to a Toxin B and antibodies that bind to at least one vegetative cell antigen (1:1 ratio)
3. Antibodies that bind to a Toxin B, antibodies that bind to at least one endospore antigen, and antibodies that bind to at least one vegetative cell antigen (1:1:1 ratio)
4. Antibodies that bind to a Toxin B
5. Antibodies that bind at least one vegetative cell antigen To examine *C. difficile* associated disease, weight loss was examined in mice administered either non-immune colostrum or bovine hyperimmune colostrum comprising the relevant antibodies or mixture of colostrum comprising the relevant antibodies.

To examine *C. difficile* associated mortality, survival was examined in mice administered either non-immune colostrum or bovine hyperimmune colostrum comprising the relevant antibodies or mixture of colostrum comprising the relevant antibodies.

As shown in FIG. 17, 4 of 5 mice that received a combination of three antibodies survived, indicating a synergistic effect of the antibodies that bind to a *Clostridium difficile* Toxin B, antibodies that bind to at least one *Clostridium difficile* vegetative cell antigen, and antibodies that bind to at least one *Clostridium difficile* endospore antigen.

This data indicates that mice administered a composition comprising antibodies that bind to a Toxin B, antibodies that bind to at least one endospore antigen, and antibodies that bind to at least one vegetative cell antigen showed delayed weight loss and increased survival compared to mice that received non-immune colostrum.

These results also indicate that antibodies that bind to *C. difficile* Toxin B alone or a combination of *C. difficile* antigens in bovine hyperimmune colostrum are effective in neutralising the activity of Toxin B in vivo and other antigens, thereby preventing damage to the gastrointestinal tract of pre-treated mice.

EXAMPLE 17

Treatment of Mice with Antibodies that Bind to Toxin B for Treating *C. difficile* Associated Disease Groups of male, 6-7 week old, C57/BL6 mice are pre-treated with an antibiotic cocktail for 7 days prior to *C. difficile* infection ($10^3$ endospores/mouse). Hyperimmune colostrum comprising antibodies that bind to Toxin B (cow #7010) is administered by oral gavage 2, 4 or 6 hours post infection. At these time points, the drinking water is replaced with colostrum. Mice are kept on colostrum during the course of the trial and monitored for weight loss and survival. Mice are humanely sacrificed in accordance with animal ethics.

Further experiments are conducted wherein the hyperimmune colostrum is administered 8, 10, 12 or 24 hours post-infection.

EXAMPLE 18

Pre-Treatment of Mice with Combinations of Antibodies that Bind to *C. difficile* Antigens for Treating *C. difficile* Associated Disease Combinations of antibodies that bind to *C. difficile* are examined for their ability to prevent measures of *C. difficile* associated disease such as morbidity and mortality in mice, as described above.

Following individual testing, the different combinations and ratios are as follows:

Antibodies that bind a Toxin B and antibodies that bind to at least one endospore antigen (1:1 ratio)

Antibodies that bind a Toxin B and antibodies that bind to at least one endospore antigen (2:1 ratio)

Antibodies that bind to a Toxin B, antibodies that bind to at least one endospore antigen, and antibodies that bind to at least one vegetative cell antigen (1:1:1 ratio)

Antibodies that bind to a Toxin B, antibodies that bind to at least one endospore antigen, and antibodies that bind to at least one vegetative cell antigen (2:1:1 ratio)

Antibodies that bind to a Toxin B, antibodies that bind to at least one endospore antigen, and antibodies that bind to at least one vegetative cell antigen (3:1:1 ratio)

Antibodies that bind to a Toxin B, antibodies that bind to at least one endospore antigen, and antibodies that bind to at least one vegetative cell antigen (4:1:1 ratio)

Antibodies that bind to a Toxin B, antibodies that bind to at least one endospore antigen, and antibodies that bind to at least one vegetative cell antigen (5:1:1 ratio)

Antibodies that bind to a Toxin B, antibodies that bind to at least one endospore antigen, and antibodies that bind to at least one vegetative cell antigen (6:1:1 ratio)

Antibodies that bind to a Toxin B, antibodies that bind to at least one endospore antigen, and antibodies that bind to at least one vegetative cell antigen (7:1:1 ratio)

Antibodies that bind to a Toxin B, antibodies that bind to at least one endospore antigen, and antibodies that bind to at least one vegetative cell antigen (8:1:1 ratio)

Antibodies that bind to a Toxin B and antibodies that bind to at least one vegetative cell antigen (2:1 ratio)

Antibodies that bind to at least one vegetative cell antigen and antibodies that bind to a S-layer protein (1:1 ratio)

Antibodies that bind to at least one vegetative cell antigen and antibodies that bind to at least one endospore antigen (1:1 ratio)

EXAMPLE 19

Treatment of Mice with Combinations of Antibodies that Bind to *C. difficile* Antigens for Treating *C. difficile* Associated Disease Combinations of antibodies of Example 18 that are effective for preventing measures of *C. difficile* associated disease such as morbidity and mortality in mice, are tested for their effectiveness at treating measures of *C. difficile* associated disease such as morbidity and mortality in mice. In brief, groups of male, 6-7 week old, C57/BL6 mice are pre-treated with an antibiotic cocktail for 7 days prior to *C. difficile* infection ($10^3$ endospores/mouse). Hyperimmune colostrum comprising antibodies that bind to antigens, and combinations of antibodies that bind to *C. difficile*, are administered by oral gavage 2, 4 or 6 hours post infection. At these time points, the drinking water is replaced with colostrum. Mice are kept on colostrum during the course of the trial and monitored for weight loss and survival. Mice are humanely sacrificed in accordance with animal ethics.

EXAMPLE 20

Pre-Treatment of Mice with Antibodies that Bind to *C. difficile* Antigens for Inhibiting Transmission of *C. difficile*

Antibodies and combinations of antibodies of that are effective for preventing and/or treating measures of *C. difficile* associated disease such as morbidity and mortality in mice are tested for their effectiveness at preventing transmission *C. difficile* to naïve animals. This experiment aims to mimic a human infection in a clinical setting whereby patients contract *C. difficile* from the environment. In brief, naïve, antibiotic-treated mice are placed in a cage that previously contained mice that were pre-treated with endospore or vegetative cell colostrum prior to infection with *C. difficile*, and the naïve mice exposed to the cages are monitored for *C. difficile* colonisation, weight loss and survival. Mice are humanely sacrificed in accordance with animal ethics. The ability of colostrum-derived antibodies that bind to antigens as described herein reduce transmission by binding to toxins, spores and/or vegetative cells is determined.

EXAMPLE 21

Pre-Treatment of Mice with Antibodies that Bind to *C. difficile* Antigens for Inhibiting Recurrence of *C. difficile* Infection To examine whether colostrum-derived antibodies inhibit recurrent *C. difficile* associated disease, mice are infected with *C. difficile* and then treated with vancomycin. Following recovery from infection, vancomycin treatment is ceased and the mice are administered either non-immune or *C. difficile* antigen-specific colostrum, and monitored for relapse of *C. difficile* associated disease.

EXAMPLE 22

Administration of Antibodies that Bind to *C. difficile* Toxin B or Administration Combinations of Antibodies that Bind to *C. difficile* Antigens Following Infection Reduces *C. difficile* Associated Weight Loss and *C. difficile* Associated Gastrointestinal Damage FIG. 18 shows that mice that received a combination of colostrum (Toxin B, vegetative cell and endospore at a ratio of 1:1:1) following infection and survived the infection showed healthier colons, and 70% of treated mice show prevention of damage to the GI tract, compared to those that received the combination and did not survive.

This data indicates that mice administered a composition comprising antibodies that bind to a Toxin B, antibodies that bind to at least one endospore antigen, and antibodies that bind to at least one vegetative cell antigen following infection showed reduced gastrointestinal damage.

EXAMPLE 23

Administration of Antibodies that Bind to *C. difficile* Toxin B are Effective for the Treatment of *C. difficile* Associated Weight Loss and *C. difficile* Associated Mortality FIG. 19 shows hyperimmune colostrum derived from cows vaccinated with recombinant Toxin B derived from *C. difficile* comprises antibodies that are effective in treating weight loss associated with *C. difficile* infection, and are highly effective in preventing *C. difficile* associated mortality when administered following infection with *C. difficile*.

The claims defining the invention are as follows:

1. A composition comprising mammalian hyperimmune colostrum for use in the treatment and/or prophylaxis of at least one symptom of *Clostridium difficile* associated disease, wherein the hyperimmune colostrum comprise:

a) antibodies that bind to a *Clostridium difficile* Toxin B; and b) antibodies that bind to at least one *Clostridium difficile* vegetative cell antigen, and/or antibodies that bind to at least one *Clostridium difficile* endospore antigen, wherein the antibodies that bind to at least one *Clostridium difficile* vegetative cell antigen are raised against a vaccine comprising vegetative cells or an S-layer preparation of a first strain of *Clostridium difficile*, and wherein the antibodies that bind to at least one *Clostridium difficile* endospore antigen are raised against a vaccine comprising endospores of a first strain of *Clostridium difficile*.

2. The composition according to claim 1 wherein the antibodies that bind to a *Clostridium difficile* Toxin B are raised against a vaccine comprising a first strain Toxin B of a first strain of *Clostridium difficile*.

3. The composition according to claim 2 wherein the vaccine comprises *Clostridium difficile* strain 630 Toxin B.

4. The composition according to claim 2 wherein the antibodies that bind to a *Clostridium difficile* Toxin B bind to a Toxin B of a second strain of *Clostridium difficile*.

5. The composition according to claim 1 wherein the antibodies bind to S-layer protein A (SlpA).

6. The composition according to claim 1 wherein the antibodies that bind to at least one *Clostridium difficile* vegetative cell antigen bind to at least one *Clostridium difficile* vegetative cell antigen of a second strain of *Clostridium difficile*.

7. The composition according to claim 1 wherein the vaccine comprises endospores of a first strain of *Clostridium difficile* comprises *Clostridium difficile* strain KI endospores.

8. The composition according to claim 1 wherein the antibodies bind to exosporium proteins.

9. The composition according to claim 1 wherein the antibodies that bind to at least one *Clostridium difficile* endospore antigen bind to at least one endospore antigen of a second strain of *Clostridium difficile*.

10. The composition according to claim 1, wherein the antibodies that bind to a *Clostridium difficile* Toxin B, antibodies that bind to at least one *Clostridium difficile* vegetative cell antigen, and antibodies that bind to at least one *Clostridium difficile* endospore antigen are present in a 1:1:1 ratio.

11. The composition according to claim 1 wherein the antibodies that bind to a *Clostridium difficile* Toxin B, antibodies that bind to at least one *Clostridium difficile* vegetative cell antigen, and antibodies that bind to at least one *Clostridium difficile* endospore antigen are present in a 2:1:1 ratio.

12. The composition according to claim 1 wherein the antibodies that bind to a *Clostridium difficile* Toxin B, antibodies that bind to at least one *Clostridium difficile* vegetative cell antigen, and antibodies that bind to at least one *Clostridium difficile* endospore antigen are present in a 3:1:1 ratio.

13. The composition according to claim 1 wherein the antibodies that bind to a *Clostridium difficile* Toxin B, antibodies that bind to at least one *Clostridium difficile* vegetative cell antigen, and antibodies that bind to at least one *Clostridium difficile* endospore antigen are present in a 8:1:1 ratio.

14. The composition according to claim 1 wherein the hyperimmune colostrum is bovine hyperimmune colostrum.

15. The composition according to claim 1 wherein the hyperimmune colostrum is prepared by vaccination of a first lot of one or more mammals with a vaccine comprising *Clostridium difficile* Toxin B, and vaccination of a second lot of one or more mammals with a vaccine comprising *Clostridium difficile* vegetative cells and/or vaccination of a third lot of one or more mammals with a vaccine comprising *Clostridium difficile* endospores, and subsequently blending the hyperimmune colostrum from the lots.

16. The composition according to claim 1, wherein the composition is formulated for oral administration.

17. The composition according to claim 1, wherein the composition is formulated at a dose of about 30 mg to about 15000 mg of composition.

18. The composition according to claim 17 wherein the composition is formulated at a dose of about 1800 mg of composition.

19. The composition according to claim 1, wherein the at least one symptom of *Clostridium difficile* associated disease is selected from diarrhea, abdominal pain, fever, loss of appetite, pseudomembranous colitis, cytotoxic megacolon, *C. difficile* colonisation, weight loss, cytotoxicity, gastrointestinal damage, histopathologic change in the gastrointestinal tract, faecal shedding of *C. difficile* spores, and *C. difficile* associated mortality.

20. A method for the treatment and/or prophylaxis of at least one symptom of *Clostridium difficile* associated disease in a subject, said method comprising administering to the subject a therapeutically effective amount of the composition of claim 1.

21. The method according to claim 20 wherein the antibodies that bind to a *Clostridium difficile* Toxin B are raised against a vaccine comprising a first strain Toxin B of a first strain of *Clostridium difficile*.

22. The method according to claim 21 wherein the vaccine comprises *Clostridium difficile* strain 630 Toxin B.

23. The method according to claim 21 wherein the antibodies that bind to a *Clostridium difficile* Toxin B bind to a Toxin B of a second strain of *Clostridium difficile*.

24. The method according to claim 20 wherein the antibodies bind to S-layer protein A (SlpA).

25. The method according to claim 20 wherein the antibodies that bind to at least one *Clostridium difficile* vegetative cell antigen bind to at least one *Clostridium difficile* vegetative cell antigen of a second strain of *Clostridium difficile*.

26. The method according to claim 20 wherein the vaccine comprising endospores of a first strain of *Clostridium difficile* comprises *Clostridium difficile* strain KI endospores.

27. The method according to claim 20 wherein the antibodies bind to exosporium proteins.

28. A method according to claim 20 wherein the antibodies that bind to at least one *Clostridium difficile* endospore antigen bind to at least one endospore antigen of a second strain of *Clostridium difficile*.

29. The method according to claim 20 wherein the hyperimmune colostrum is bovine hyperimmune colostrum.

30. The method according to claim 29 wherein the hyperimmune colostrum is prepared by vaccination of a first lot of one or more mammals with a vaccine comprising *Clostridium difficile* Toxin B, and vaccination of a second lot of one or more mammals with a vaccine comprising *Clostridium difficile* vegetative cells and/or vaccination of a third lot of one or more mammals with a vaccine comprising *Clostridium difficile* endospores, and subsequently blending the hyperimmune colostrum from the lots.

31. The composition according to claim 20, wherein the composition is formulated for oral administration.

32. The method according to claim 20, wherein the composition is administered at a dose of about 30 mg to about 15000 mg per day.

33. The method according to claim 32 wherein the composition is administered at a dose of about 1800 mg per day.

34. The method according to claim 20, wherein the at least one symptom of *Clostridium difficile* associated disease is selected from diarrhea, abdominal pain, fever, loss of appetite, pseudomembranous colitis, cytotoxic megacolon, *C. difficile* colonisation, weight loss, cytotoxicity, gastrointestinal damage, histopathologic change in the gastrointestinal tract, faecal shedding of *C. difficile* spores, and *C. difficile* associated mortality.

35. The method according to claim 20, wherein the antibodies that bind to a *Clostridium difficile* Toxin B, antibodies that bind to at least one *Clostridium difficile* vegetative cell antigen, and antibodies that bind to at least one *Clostridium difficile* endospore antigen are present in a 1:1:1 ratio.

36. The method according to claim 20, wherein the antibodies that bind to a *Clostridium difficile* Toxin B, antibodies that bind to at least one *Clostridium difficile* vegetative cell antigen, and antibodies that bind to at least one *Clostridium difficile* endospore antigen are present in a 2:1:1 ratio.

37. The method according to claim 20, wherein the antibodies that bind to a *Clostridium difficile* Toxin B, antibodies that bind to at least one *Clostridium difficile* vegetative cell antigen, and antibodies that bind to at least one *Clostridium difficile* endospore antigen are present in a 3:1:1 ratio.

38. The method according to claim 20, wherein the antibodies that bind to a *Clostridium difficile* Toxin B, antibodies that bind to at least one *Clostridium difficile* vegetative cell antigen, and antibodies that bind to at least one *Clostridium difficile* endospore antigen are present in a 8:1:1 ratio.

* * * * *